United States Patent
Essaddam et al.

(10) Patent No.: US 12,415,179 B2
(45) Date of Patent: Sep. 16, 2025

(54) PROCESS FOR RECOVERING AND REUSING DEPOLYMERIZATION CATALYST

(71) Applicant: 9449710 CANADA INC., Terrebonne (CA)

(72) Inventors: Fares Essaddam, Bois-des-Filion (CA); Hatem Essaddam, Sainte-Thérése (CA); Ramzi Zarrougui, Sainte-Thérése (CA)

(73) Assignee: 9449710 CANADA INC., Terrebonne (CA)

( * ) Notice: Subject to any disclaimer, the term of this patent is extended or adjusted under 35 U.S.C. 154(b) by 0 days.

(21) Appl. No.: 18/611,495

(22) Filed: Mar. 20, 2024

(65) Prior Publication Data

US 2024/0382941 A1    Nov. 21, 2024

Related U.S. Application Data

(63) Continuation of application No. 18/446,403, filed on Aug. 8, 2023, now abandoned, which is a continuation of application No. 18/066,136, filed on Dec. 14, 2022, now abandoned, which is a continuation of application No. 16/821,866, filed on Mar. 17, 2020, now Pat. No. 11,554,366.

(60) Provisional application No. 62/821,264, filed on Mar. 20, 2019.

(51) Int. Cl.

| | |
|---|---|
| *B01J 31/40* | (2006.01) |
| *B01J 20/284* | (2006.01) |
| *B01J 20/34* | (2006.01) |
| *B01J 31/02* | (2006.01) |
| *B01J 38/52* | (2006.01) |
| *C07C 27/26* | (2006.01) |
| *C08J 11/24* | (2006.01) |
| *C07C 31/30* | (2006.01) |
| *C07C 69/82* | (2006.01) |

(52) U.S. Cl.
CPC ............. *B01J 31/40* (2013.01); *B01J 20/284* (2013.01); *B01J 20/3475* (2013.01); *B01J 31/0202* (2013.01); *B01J 38/52* (2013.01); *C07C 27/26* (2013.01); *C08J 11/24* (2013.01); *C07C 31/30* (2013.01); *C07C 69/82* (2013.01)

(58) Field of Classification Search
CPC . B01J 20/08; B01J 20/103; B01J 20/18; B01J 20/262; B01J 20/28057; B01J 20/28078; B01J 20/284; B01J 20/3408; B01J 20/3425; B01J 20/3433; B01J 20/3475; B01J 31/0202; B01J 31/40; B01J 38/52; B01J 2220/42; C07C 27/26; C07C 29/76; C07C 31/30; C07C 67/03; C07C 69/82; Y02P 20/52; Y02P 20/584
See application file for complete search history.

(56) References Cited

U.S. PATENT DOCUMENTS

| | | |
|---|---|---|
| 3,501,420 A | 3/1970 | Stevenson et al. |
| 5,495,061 A | 2/1996 | Kulprathipanja |
| 5,770,778 A | 6/1998 | Naujokas |
| 9,127,136 B1 | 9/2015 | Bell et al. |
| 11,554,366 B2 | 1/2023 | Essaddam et al. |
| 2005/0096482 A1 | 5/2005 | Tamada et al. |
| 2017/0008826 A1 | 1/2017 | Essaddam |
| 2023/0374249 A1 | 11/2023 | Essaddam et al. |

FOREIGN PATENT DOCUMENTS

| | | |
|---|---|---|
| CN | 106629796 A | 5/2017 |
| FR | 1081681 A | 12/1954 |
| JP | H08157402 A | 6/1996 |
| JP | 2003048866 A | 2/2003 |
| WO | WO-2020188354 A1 | 9/2020 |

OTHER PUBLICATIONS

Bae et al., The Characteristics of PET Micro Fiber Fabrics Decomposed dy Sodium Ethylene glycol Solution. Journal of the Korean Home Economics Association 36(8):95-104 (1998) (English Abstract).
EP20774082.0 Extended European Search Report dated Jun. 7, 2023.
PCT/IB2020/000192 International Search Report and Written Opinion dated Jul. 2, 2020.
U.S. Appl. No. 16/821,866 Office Action dated Mar. 2, 2022.

*Primary Examiner* — Brian A McCaig
(74) *Attorney, Agent, or Firm* — WILSON SONSINI GOODRICH & ROSATI

(57) ABSTRACT

The present disclosure relates to the recovery of an alkoxide catalyst used in a process depolymerizing a polyester to form a diacid or diester and a diol. The present disclosure also relates to the recovery of an alkoxide catalyst used in a process depolymerizing polyethylene terephthalate to form dimethyl terephthalate and mono ethylene glycol.

22 Claims, No Drawings

PROCESS FOR RECOVERING AND REUSING DEPOLYMERIZATION CATALYST

CROSS-REFERENCE

This application is a continuation of U.S. patent application Ser. No. 18/446,403, filed Aug. 8, 2023, which is a continuation of U.S. patent application Ser. No. 18/066,136, filed Dec. 14, 2022, which is a continuation of U.S. patent application Ser. No. 16/821,866, filed Mar. 17, 2020, now U.S. Pat. No. 11,554,366, issued Jan. 17, 2023, which claims the benefit of U.S. Provisional Application Ser. No. 62/821,264, filed Mar. 20, 2019, which are hereby incorporated by reference in their entirety.

FIELD OF THE INVENTION

The present disclosure relates to a recovery of an alkoxide from an alkoxide containing mother liquor. The present disclosure also relates to a process for purifying a diol mother liquor. The present disclosure also relates to a process for depolymerizing a polyester wherein the process uses an alkoxide recovered from an alkoxide containing mother liquor.

BACKGROUND OF THE INVENTION

The polyethylene terephthalate (PET) bottle resin market has been growing strongly as PET resins have replaced glass in carbonated soft drink, bottled water and food containers.

Dimethyl terephthalate (DMT) is primarily used in the manufacture of polyethylene terephthalate (PET) for fiber, film, container plastics, and specialty plastics applications.

The largest polyester sector is the fibers market where it is used to make clothes, home textiles such as sheets and curtains, carpets and rugs, and industrial products such as tire cord, seat belts, hoses and ropes. PET film is utilized in electrical applications such as dielectric metal foil capacitors and for food packaging.

SUMMARY OF THE INVENTION

Described herein is a process for the recovery of an alkoxide from an alkoxide containing mother liquor; the process comprising: (i) an adsorption cycle; (ii) a wash cycle; and (iii) a desorption cycle. In some embodiments, the adsorption cycle, wash cycle, and desorption cycle are performed sequentially. In some embodiments, the adsorption cycle, and/or wash cycle and/or desorption cycle are performed continuously. In some embodiments, the alkoxide containing mother liquor is obtained from a process of depolymerizing a polyester to form an organic diacid and a diol. In some embodiments, the alkoxide containing mother liquor is obtained from a process of depolymerizing a polyester to form a diester and a diol. In some embodiments, the alkoxide containing mother liquor is obtained from a process of depolymerizing polyethylene terephthalate (PET) to form a terephthalate and/or an isophthalate, and mono ethylene glycol (MEG). In some embodiments, the alkoxide containing mother liquor further comprises a diol. In some embodiments, the diol is mono ethylene glycol (MEG). In some embodiments, the adsorption cycle comprises contacting the alkoxide containing mother liquor with an adsorbent, thereby adsorbing the alkoxide. In some embodiments, the adsorption cycle comprises eluting the alkoxide containing mother liquor through an adsorbent, thereby adsorbing the alkoxide. In some embodiments, the eluting through the adsorbent is performed 1 to 20 times. In some embodiments, the eluting through the adsorbent is performed 1 to 10 times. In some embodiments, the eluting through the adsorbent is performed 1 to 5 times. In some embodiments, the eluting through the adsorbent is performed 1 to 3 times. In some embodiments, the eluting through the adsorbent is performed until at least about 30% of the alkoxide is adsorbed. In some embodiments, the eluting through the adsorbent is performed until at least about 90% of the alkoxide is adsorbed. In some embodiments, the eluting through the adsorbent is performed until at least about 95% of the alkoxide is adsorbed. In some embodiments, the eluting through the adsorbent is performed until at least about 99% of the alkoxide is adsorbed. In some embodiments, the adsorbent is silica gel, a silicate derivative, $Al_2O_3$, polymeric alumina, zeolites, activated carbon, polysulfones, polysulfates, polycarboxylates, or any combinations thereof. In some embodiments, the adsorbent is silica gel with pore size between about 10 μm and about 800 μm. In some embodiments, the adsorbent is silica gel with specific surface area between about 20 $m^2/g$ and about 1000 $m^2/g$. In some embodiments, the adsorbent is basic alumina, neutral alumina, or acidic alumina. In some embodiments, the adsorbent is a mixture of alumina and silica gel. In some embodiments, the adsorbent is a mixture of zeolites and silica gel. In some embodiments, the wash cycle comprises washing the adsorbent with a wash solvent, thereby eliminating ester salts, pigments, and dyes adsorbed during the adsorption cycle. In some embodiments, the wash cycle is co-current or counter current. In some embodiments, the wash cycle is counter current. In some embodiments, the washing is performed 1 to 20 times. In some embodiments, the washing is performed 1 to 10 times. In some embodiments, the washing is performed 1 to 5 times. In some embodiments, the washing is performed 1 to 3 times. In some embodiments, the washing is performed until at most about 30% of the alkoxide is desorbed from the adsorbent. In some embodiments, the washing is performed until at most about 10% of the alkoxide is desorbed from the adsorbent. In some embodiments, the washing is performed until at most about 5% of the alkoxide is desorbed from the adsorbent. In some embodiments, the washing is performed until at most about 1% of the alkoxide is desorbed from the adsorbent. In some embodiments, the wash solvent is a polar protic solvent. In some embodiments, the wash solvent is a polar aprotic solvent. In some embodiments, the wash solvent is an apolar aprotic solvent. In some embodiments, the wash solvent is an alcoholic solvent. In some embodiments, the wash solvent is methanol. In some embodiments, the desorption cycle comprises washing the adsorbent with a desorption solvent, thereby obtaining a mixture comprising the alkoxide and the desorption solvent. In some embodiments, the washing to obtain the mixture comprising the alkoxide and the desorption solvent is performed 1 to 20 times. In some embodiments, the washing to obtain the mixture comprising the alkoxide and the desorption solvent is performed 1 to 10 times. In some embodiments, the washing to obtain the mixture comprising the alkoxide and the desorption solvent is performed 1 to 5 times. In some embodiments, the washing to obtain the mixture comprising the alkoxide and the desorption solvent is performed 1 to 3 times. In some embodiments, the washing to obtain the mixture comprising the alkoxide and the desorption solvent is performed until at least about 30% of the alkoxide is desorbed from the adsorbent. In some embodiments, the washing to obtain the mixture comprising the alkoxide and the desorption solvent is performed until at least about 90% of the alkoxide is desorbed from the adsorbent. In some embodiments, the washing to obtain the mixture comprising the alkoxide and the desorption solvent is performed until at least about 95% of the alkoxide is desorbed from the adsorbent. In some embodiments, the washing to obtain the mixture comprising the alkoxide and the desorption solvent is performed until at least about 99% of the alkoxide is desorbed from the adsorbent. In some embodiments, the desorption solvent is a polar protic solvent. In some embodiments, the desorption solvent is a polar aprotic solvent. In some embodiments, the desorption solvent is an apolar aprotic solvent. In some embodiments, the desorption solvent is an alcoholic solvent. In some embodiments, the desorption solvent is methanol. In some embodiments, a portion of the desorption solvent in the mixture comprising the alkoxide and the desorption solvent is subsequently removed. In some embodiments, the final concentration of the alkoxide in the desorption solvent is between about 0.1 wt-% to about 100 wt-%. In some embodiments, the alkoxide in the desorption solvent is re-used in a process of depolymerizing a polyester to form an organic diacid and a diol. In some embodiments, the alkoxide in the desorption solvent is re-used in a process of depolymerizing a polyester to form a diester and a diol. In some embodiments, the alkoxide in the desorption solvent is re-used in a process of depolymerizing polyethylene terephthalate (PET) to form a terephthalate and/or an isophthalate, and mono ethylene glycol (MEG). In some embodiments, the alkoxide is an alkali metal alkoxide, an alkaline earth metal alkoxide, a metal alkoxide, an ammonium alkoxide, or any combinations thereof. In some embodiments, the alkoxide is sodium methoxide, sodium glycoxide, potassium ethoxide, aluminum tri-n-propoxide, tetrabutylammonium methoxide, or any combinations thereof. In some embodiments, the alkoxide is sodium methoxide. In some embodiments, the alkoxide is sodium glycoxide. In some embodiments, the process further comprises (iv) a regeneration cycle. In some embodiments, the regeneration cycle comprises washing the adsorbent with an acid, thereby regenerating the adsorbent. In some embodiments, the washing is performed 1 to 20 times. In some embodiments, the washing is performed 1 to 10 times. In some embodiments, the washing is performed 1 to 5 times. In some embodiments, the washing is performed 1 to 3 times. In some embodiments, the acid is acetic acid, formic acid, hydrochloric acid, sulfuric acid, phosphoric acid, or any combinations thereof. In some embodiments, the acid is acetic acid. In some embodiments, the acid is formic acid. In some embodiments, one regeneration cycle is performed for every 50 (i) adsorption cycle/(ii) wash cycle/(iii) desorption cycle. In some embodiments, one regeneration cycle is performed for every 20 (i) adsorption cycle/(ii) wash cycle/(iii) desorption cycle. In some embodiments, one regeneration cycle is performed for every 10 (i) adsorption cycle/(ii) wash cycle/(iii) desorption cycle. In some embodiments, one regeneration cycle is performed for every 5 (i) adsorption cycle/(ii) wash cycle/(iii) desorption cycle.

Also disclosed herein is a process for purifying a diol mother liquor; the process comprising: (i) an adsorption cycle; (ii) a wash cycle; and (iii) a desorption cycle. In some embodiments, the diol is mono ethylene glycol (MEG). In some embodiments, the adsorption cycle, wash cycle, and desorption cycle are performed sequentially. In some embodiments, the adsorption cycle and/or wash cycle and/or desorption cycle are performed continuously. In some embodiments, the diol mother liquor is obtained from a process of depolymerizing a polyester to form an organic diacid and a diol. In some embodiments, the diol mother liquor is obtained from a process of depolymerizing a polyester to form a diester and a diol. In some embodiments, the diol mother liquor is obtained from a process of depolymerizing polyethylene terephthalate (PET) to form a terephthalate and/or an isophthalate, and mono ethylene glycol (MEG). In some embodiments, the diol mother liquor further comprises an alkoxide. In some embodiments, the adsorption cycle comprises contacting the diol mother liquor through an adsorbent, thereby adsorbing the alkoxide. In some embodiments, the adsorption cycle comprises eluting the diol mother liquor through an adsorbent, thereby adsorbing the alkoxide. In some embodiments, the eluting through the adsorbent is performed 1 to 20 times. In some embodiments, the eluting through the adsorbent is performed 1 to 10 times. In some embodiments, the eluting through the adsorbent is performed 1 to 5 times. In some embodiments, the eluting through the adsorbent is performed 1 to 3 times. In some embodiments, the eluting through the adsorbent is performed until at least about 30% of the alkoxide is adsorbed. In some embodiments, the eluting through the adsorbent is performed until at least about 90% of the alkoxide is adsorbed. In some embodiments, the eluting through the adsorbent is performed until at least about 95% of the alkoxide is adsorbed. In some embodiments, the eluting through the adsorbent is performed until at least about 99% of the alkoxide is adsorbed. In some embodiments, the adsorbent is silica gel, a silicate derivative, $Al_2O_3$, polymeric alumina, zeolites, activated carbon, polysulfones, polysulfates, polycarboxylates, or any combinations thereof. In some embodiments, the adsorbent is silica gel with pore size between about 10 μm and about 800 μm. In some embodiments, the adsorbent is silica gel with specific surface area between about 20 $m^2/g$ and about 1000 $m^2/g$. In some embodiments, the adsorbent is basic alumina, neutral alumina, or acidic alumina. In some embodiments, the adsorbent is a mixture of alumina and silica gel. In some embodiments, the adsorbent is a mixture of zeolites and silica gel. In some embodiments, the wash cycle comprises washing the adsorbent with a wash solvent, thereby eliminating ester salts, pigments, and dyes adsorbed during the adsorption cycle. In some embodiments, the wash cycle is co-current or counter current. In some embodiments, the wash cycle is counter current. In some embodiments, the washing is performed 1 to 20 times. In some embodiments, the washing is performed 1 to 10 times. In some embodiments, the washing is performed 1 to 5 times. In some embodiments, the washing is performed 1 to 3 times. In some embodiments, the washing is performed until at most about 30% of the alkoxide is desorbed from the adsorbent. In some embodiments, the washing is performed until at most about 10% of the alkoxide is desorbed from the adsorbent. In some embodiments, the washing is performed until at most about 5% of the alkoxide is desorbed from the adsorbent. In some embodiments, the washing is performed until at most about 1% of the alkoxide is desorbed from the adsorbent. In some embodiments, the wash solvent is a polar protic solvent. In some embodiments, the wash solvent is a polar aprotic solvent. In some embodiments, the wash solvent is an apolar aprotic solvent. In some embodiments, the wash solvent is an alcoholic solvent. In some embodiments, the wash solvent is methanol. In some embodiments, the desorption cycle comprises washing the adsorbent with a desorption solvent, thereby obtaining a mixture comprising the alkoxide and the desorption solvent. In some embodiments, the washing to obtain the mixture comprising the alkoxide and the desorption solvent is performed 1 to 20 times. In some embodiments, the washing to obtain the mixture comprising the alkoxide and the desorption solvent is performed 1 to 10 times. In some embodiments, the washing to obtain the mixture comprising the alkoxide and the desorption solvent is performed 1 to 5 times. In some embodiments, the washing to obtain the mixture comprising the alkoxide and the desorption solvent is performed 1 to 3 times. In some embodiments, the washing to obtain the mixture comprising the alkoxide and the desorption solvent is performed until at least about 30% of the alkoxide is desorbed from the adsorbent. In some embodiments, the washing to obtain the mixture comprising the alkoxide and the desorption solvent is performed until at least about 90% of the alkoxide is desorbed from the adsorbent. In some embodiments, the washing to obtain the mixture comprising the alkoxide and the desorption solvent is performed until at least about 95% of the alkoxide is desorbed from the adsorbent. In some embodiments, the washing to obtain the mixture comprising the alkoxide and the desorption solvent is performed until at least about 99% of the alkoxide is desorbed from the adsorbent. In some embodiments, the desorption solvent is a polar protic solvent. In some embodiments, the desorption solvent is a polar aprotic solvent. In some embodiments, the desorption solvent is an apolar aprotic solvent. In some embodiments, the desorption solvent is an alcoholic solvent. In some embodiments, the desorption solvent is methanol. In some embodiments, a portion of the desorption solvent in the mixture comprising the alkoxide and the desorption solvent is subsequently removed. In some embodiments, the final concentration of the alkoxide in the desorption solvent is between about 0.1 wt-% to about 100 wt-%. In some embodiments, the alkoxide in the desorption solvent is re-used in a process of depolymerizing a polyester to form an organic diacid and a diol. In some embodiments, the alkoxide in the desorption solvent is re-used in a process of depolymerizing a polyester to form a diester and a diol. In some embodiments, the alkoxide in the desorption solvent is re-used in a process of depolymerizing polyethylene terephthalate (PET) to form a terephthalate and/or an isophthalate and mono ethylene glycol (MEG). In some embodiments, the alkoxide is an alkali metal alkoxide, an alkaline earth metal alkoxide, a metal alkoxide, an ammonium alkoxide, or any combinations thereof. In some embodiments, the alkoxide is sodium methoxide, sodium glycoxide, potassium ethoxide, aluminum tri-n-propoxide, tetrabutylammonium methoxide, or any combinations thereof. In some embodiments, the alkoxide is sodium methoxide. In some embodiments, the alkoxide is sodium glycoxide. In some embodiments, the process further comprises (iv) a regeneration cycle. In some embodiments, the regeneration cycle comprises washing the adsorbent with an acid, thereby regenerating the adsorbent. In some embodiments, the washing is performed 1 to 20 times. In some embodiments, the washing is performed 1 to 10 times. In some embodiments, the washing is performed 1 to 5 times. In some embodiments, the washing is performed 1 to 3 times. In some embodiments, the acid is acetic acid, formic acid, hydrochloric acid, sulfuric acid, phosphoric acid, or any combinations thereof. In some embodiments, the acid is acetic acid. In some embodiments, the acid is formic acid. In some embodiments, one regeneration cycle is performed for every 50 (i) adsorption cycle/(ii) wash cycle/(iii) desorption cycle. In some embodiments, one regeneration cycle is performed for every 20 (i) adsorption cycle/(ii) wash cycle/(iii) desorption cycle. In some embodiments, one regeneration cycle is performed for every 10 (i) adsorption cycle/(ii) wash cycle/(iii) desorption cycle. In some embodiments, one regeneration cycle is performed for every 5 (i) adsorption cycle/(ii) wash cycle/(iii) desorption cycle.

A process for depolymerizing a polyester; the process comprising admixing the polyester with a mixture comprising an alkoxide; wherein the alkoxide is recovered from an alkoxide containing mother liquor using a process comprising: (i) an adsorption cycle; (ii) a wash cycle; and (iii) a desorption cycle. In some embodiments, the process for depolymerizing the polyester results in the formation of an organic diacid and a diol. In some embodiments, the process for depolymerizing the polyester results in the formation of a diester and a diol. In some embodiments, the polyester is polyethylene terephthalate (PET). In some embodiments, the process for depolymerizing polyethylene terephthalate (PET) results in the formation of a terephthalate and/or isophthalate, and mono ethylene glycol (MEG). In some embodiments, the mixture comprising an alkoxide further comprises a solvent. In some embodiments, the solvent is methanol, ethanol, n-propanol, isopropanol, t-butanol, ethylene glycol, glycerol, cyclohexane-1,4-dimethanol, phenol, benzyl alcohol, or any combinations thereof. In some embodiments, the solvent is methanol. In some embodiments, the adsorption cycle, wash cycle, and desorption cycle are performed sequentially. In some embodiments, the adsorption cycle and/or wash cycle and/or desorption cycle are performed continuously. In some embodiments, the alkoxide containing mother liquor is obtained from a process of depolymerizing a polyester to form an organic diacid and a diol. In some embodiments, the alkoxide containing mother liquor is obtained from a process of depolymerizing a polyester to form a diester and a diol. In some embodiments, the alkoxide containing mother liquor is obtained from a process of depolymerizing polyethylene terephthalate (PET) to form a terephthalate and/or isophthalate, and mono ethylene glycol (MEG). In some embodiments, the alkoxide containing mother liquor further comprises a diol. In some embodiments, the alkoxide containing mother liquor further comprises mono ethylene glycol (MEG). In some embodiments, the adsorption cycle comprises contacting the alkoxide containing mother liquor through an adsorbent, thereby adsorbing the alkoxide. In some embodiments, the adsorption cycle comprises eluting the alkoxide containing mother liquor through an adsorbent, thereby adsorbing the alkoxide. In some embodiments, the eluting through the adsorbent is performed 1 to 20 times. In some embodiments, the eluting through the adsorbent is performed 1 to 10 times. In some embodiments, the eluting through the adsorbent is performed 1 to 5 times. In some embodiments, the eluting through the adsorbent is performed 1 to 3 times. In some embodiments, the eluting through the adsorbent is performed until at least about 30% of the alkoxide is adsorbed. In some embodiments, the eluting through the adsorbent is performed until at least about 90% of the alkoxide is adsorbed. In some embodiments, the eluting through the adsorbent is performed until at least about 95% of the alkoxide is adsorbed. In some embodiments, the eluting through the adsorbent is performed until at least about 99% of the alkoxide is adsorbed. In some embodiments, the adsorbent is silica gel, a silicate derivative, $Al_2O_3$, polymeric alumina, zeolites, activated carbon, polysulfones, polysulfates, polycarboxylates, or any combinations thereof. In some embodiments, the adsorbent is silica gel with pore size between about 10 μm and about 800 μm. In some embodiments, the adsorbent is silica gel with specific surface area between about 20 $m^2$/g and about 1000 $m^2$/g. In some embodiments, the adsorbent is basic alumina, neutral alumina, or acidic alumina. In some embodiments, the adsorbent is a mixture of alumina and silica gel. In some embodiments, the adsorbent is a mixture of zeolites and silica gel. In some embodiments, the wash cycle comprises washing the adsorbent with a wash solvent, thereby eliminating ester salts, pigments, and dyes adsorbed during the adsorption cycle. In some embodiments, the wash cycle is co-current or counter current. In some embodiments, the wash cycle is counter current. In some embodiments, the washing is performed 1 to 20 times. In some embodiments, the washing is performed 1 to 10 times. In some embodiments, the washing is performed 1 to 5 times. In some embodiments, the washing is performed 1 to 3 times. In some embodiments, the washing is performed until at most about 30% of the alkoxide is desorbed from the adsorbent. In some embodiments, the washing is performed until at most about 10% of the alkoxide is desorbed from the adsorbent. In some embodiments, the washing is performed until at most about 5% of the alkoxide is desorbed from the adsorbent. In some embodiments, the washing is performed until at most about 1% of the alkoxide is desorbed from the adsorbent. In some embodiments, the wash solvent is a polar protic solvent. In some embodiments, the wash solvent is a polar aprotic solvent. In some embodiments, the wash solvent is an apolar aprotic solvent. In some embodiments, the wash solvent is an alcoholic solvent. In some embodiments, the wash solvent is methanol. In some embodiments, the desorption cycle comprises washing the adsorbent with a desorption solvent, thereby obtaining a mixture comprising the alkoxide and the desorption solvent. In some embodiments, the washing to obtain the mixture comprising the alkoxide and the desorption solvent is performed 1 to 20 times. In some embodiments, the washing to obtain the mixture comprising the alkoxide and the desorption solvent is performed 1 to 10 times. In some embodiments, the washing to obtain the mixture comprising the alkoxide and the desorption solvent is performed 1 to 5 times. In some embodiments, the washing to obtain the mixture comprising the alkoxide and the desorption solvent is performed 1 to 3 times. In some embodiments, the washing to obtain the mixture comprising the alkoxide and the desorption solvent is performed until at least about 30% of the alkoxide is desorbed from the adsorbent. In some embodiments, the washing to obtain the mixture comprising the alkoxide and the desorption solvent is performed until at least about 90% of the alkoxide is desorbed from the adsorbent. In some embodiments, the washing to obtain the mixture comprising the alkoxide and the desorption solvent is performed until at least about 95% of the alkoxide is desorbed from the adsorbent. In some embodiments, the washing to obtain the mixture comprising the alkoxide and the desorption solvent is performed until at least about 99% of the alkoxide is desorbed from the adsorbent. In some embodiments, the desorption solvent is a polar protic solvent. In some embodiments, the desorption solvent is a polar aprotic solvent. In some embodiments, the desorption solvent is an apolar aprotic solvent. In some embodiments, the desorption solvent is an alcoholic solvent. In some embodiments, the desorption solvent is methanol. In some embodiments, a portion of the desorption solvent in the mixture comprising the alkoxide and the desorption solvent is subsequently removed. In some embodiments, the final concentration of the alkoxide in the desorption solvent is between about 0.1 wt-% to about 100 wt-%. In some embodiments, the alkoxide in the desorption solvent is further re-used in a process of depolymerizing a polyester to form an organic diacid and a diol. In some embodiments, the alkoxide in the desorption solvent is further re-used in a process of depolymerizing a polyester to form a diester and a diol. In some embodiments, the alkoxide in the desorption solvent is further re-used in a process of depolymerizing polyethylene terephthalate (PET) to form a terephthalate and/or an isophthalate, and mono ethylene glycol (MEG). In some embodiments, the alkoxide is alkali metal alkoxide, an alkaline earth metal alkoxide, a metal alkoxide, an ammonium alkoxide, or any combinations thereof. In some embodiments, the alkoxide is sodium methoxide, sodium glycoxide, potassium ethoxide, aluminum tri-n-propoxide, tetrabutylammonium methoxide, or any combinations thereof. In some embodiments, the alkoxide is sodium methoxide. In some embodiments, the alkoxide is sodium glycoxide. In some embodiments, the process further comprises (iv) a regeneration cycle. In some embodiments, the regeneration cycle comprises washing the adsorbent with an acid, thereby regenerating the adsorbent. In some embodiments, the washing is performed 1 to 20 times. In some embodiments, the washing is performed 1 to 10 times. In some embodiments, the washing is performed 1 to 5 times. In some embodiments, the washing is performed 1 to 3 times. In some embodiments, the acid is acetic acid, formic acid, hydrochloric acid, sulfuric acid, phosphoric acid, or any combinations thereof. In some embodiments, the acid is acetic acid. In some embodiments, the acid is formic acid. In some embodiments, one regeneration cycle is performed for every 50 (i) adsorption cycle/(ii) wash cycle/(iii) desorption cycle. In some embodiments, one regeneration cycle is performed for every 20 (i) adsorption cycle/(ii) wash cycle/(iii) desorption cycle. In some embodiments, one regeneration cycle is performed for every 10 (i) adsorption cycle/(ii) wash cycle/(iii) desorption cycle. In some embodiments, one regeneration cycle is performed for every 5 (i) adsorption cycle/(ii) wash cycle/(iii) desorption cycle.

DETAILED DESCRIPTION OF THE INVENTION

An improvement in dimethyl terephthalate (DMT) and mono ethylene glycol (MEG) production from PET recycling: due to the growing use of PET in the packaging and fiber (carpet and other textile) industries there is a need for an efficient, low energy, high yielding, and cost effective way to form DMT and MEG from PET involving the recovery and reusing of the catalyst used in the depolymerization of PET.

Disclosed herein is a process for the recovery of an alkoxide from an alkoxide containing mother liquor; the process comprising:
 (i) an adsorption cycle;
 (ii) a wash cycle; and
 (iii) a desorption cycle.

In some embodiments of the process for the recovery of an alkoxide, the adsorption cycle, wash cycle, and desorption cycle are performed sequentially. In some embodiments of the process for the recovery of an alkoxide, the adsorption cycle, and/or wash cycle and/or desorption cycle are performed continuously.

In some embodiments of the process for the recovery of an alkoxide, the alkoxide containing mother liquor is obtained from a process of depolymerizing a polyester to form an organic diacid and a diol. In some embodiments of the process for the recovery of an alkoxide, the alkoxide containing mother liquor is obtained from a process of depolymerizing a polyester to form a diester and a diol. In some embodiments of the process for the recovery of an alkoxide, the diol is mono ethylene glycol (MEG) (or ethylene glycol). In some embodiments of the process for the recovery of an alkoxide, the diol is propylene glycol. In some embodiments of the process for the recovery of an alkoxide, the diol is butylene glycol. In some embodiments of the process for the recovery of an alkoxide, the diol is 1,4-cyclohexanedimethanol (1,4-bis(hydroxymethyl)cyclohexane). In some embodiments of the process for the recovery of an alkoxide, the diol is 2,2,4,4-tetramethyl-1,3-cyclobutanediol. In some embodiments of the process for the recovery of an alkoxide, the diacid is terephthalic acid. In some embodiments of the process for the recovery of an alkoxide, the diacid is isophthalic acid. In some embodiments of the process for the recovery of an alkoxide, the diester is dimethyl terephthalate (DMT). In some embodiments of the process for the recovery of an alkoxide, the diester is dimethyl isophthalate (DMI).

In some embodiments of the process for the recovery of an alkoxide, the polyester is selected from polyethylene terephthalate (PET), poly(ethylene glycol-co-1,4-cyclohexanedimethanol terephthalate) (PETG), polyglycolide or polyglycolic acid (PGA), polylactic acid (PLA), polycaprolactone (PCL), polyhydroxybutyrate (PHB), polyethylene adipate (PEA), polybutylene succinate (PBS), poly(3-hydroxybutyrate-co-3-hydroxyvalerate) (PHBV), polybutylene terephthalate (PBT), polytrimethylene terephthalate (PTT), polyethylene naphthalate (PEN), Vectran® (polyester of 4-hydroxybenzoic acid and 6-hydroxynaphthalene-2-carboxylic acid), cutin, and any combinations thereof. In some embodiments of the process for the recovery of an alkoxide, the polyester is polyethylene terephthalate (PET). In some embodiments of the process for the recovery of an alkoxide, the polyester is poly(ethylene glycol-co-1,4-cyclohexanedimethanol terephthalate) (PETG).

In some embodiments of the process for the recovery of an alkoxide, the alkoxide containing mother liquor is obtained from a process of depolymerizing polyethylene terephthalate (PET) to form a terephthalate and/or an isophthalate, and mono ethylene glycol (MEG). In some embodiments of the process for the recovery of an alkoxide, the terephthalate is dimethyl terephthalate. In some embodiments of the process for the recovery of an alkoxide, the isophthalate is dimethyl isophthalate.

In some embodiments of the process for the recovery of an alkoxide, the alkoxide containing mother liquor further comprises a diol. In some embodiments of the process for the recovery of an alkoxide, the diol is mono ethylene glycol (MEG).

Step (i): Adsorption Cycle

In some embodiments of the process for the recovery of an alkoxide, the adsorption cycle comprises contacting the alkoxide containing mother liquor with an adsorbent, thereby adsorbing the alkoxide. In some embodiments of the process for the recovery of an alkoxide, the adsorption cycle comprises eluting the alkoxide containing mother liquor through an adsorbent, thereby adsorbing the alkoxide.

In some embodiments of the process for the recovery of an alkoxide, the eluting through the adsorbent is performed 1 to 20 times. In some embodiments of the process for the recovery of an alkoxide, the eluting through the adsorbent is performed 1 to 15 times. In some embodiments of the process for the recovery of an alkoxide, the eluting through the adsorbent is performed 1 to 10 times. In some embodiments of the process for the recovery of an alkoxide, the eluting through the adsorbent is performed 1 to 5 times. In some embodiments of the process for the recovery of an alkoxide, the eluting through the adsorbent is performed 1 to 3 times. In some embodiments of the process for the recovery of an alkoxide, the eluting through the adsorbent is performed 20 times, 19 times, 18 times, 17 times, 16 times, 15 times, 14 times, 13 times, 12 times, 11 times, 10 times, 9 times, 8 times, 7 times, 6 times, 5 times, 4 times, 3 times, 2 times, or once. In some embodiments of the process for the recovery of an alkoxide, the eluting through the adsorbent is performed until at least between about 30% and about 99% of the alkoxide is adsorbed. In some embodiments of the process for the recovery of an alkoxide, the eluting through the adsorbent is performed until at least between about 50% and about 99% of the alkoxide is adsorbed. In some embodiments of the process for the recovery of an alkoxide, the eluting through the adsorbent is performed until at least between about 80% and about 99% of the alkoxide is adsorbed. In some embodiments of the process for the recovery of an alkoxide, the eluting through the adsorbent is performed until at least between about 90% and about 99% of the alkoxide is adsorbed. In some embodiments of the process for the recovery of an alkoxide, the eluting through the adsorbent is performed until at least about 30% of the alkoxide is adsorbed. In some embodiments of the process for the recovery of an alkoxide, the eluting through the adsorbent is performed until at least about 40% of the alkoxide is adsorbed. In some embodiments of the process for the recovery of an alkoxide, the eluting through the adsorbent is performed until at least about 50% of the alkoxide is adsorbed. In some embodiments of the process for the recovery of an alkoxide, the eluting through the adsorbent is performed until at least about 60% of the alkoxide is adsorbed. In some embodiments of the process for the recovery of an alkoxide, the eluting through the adsorbent is performed until at least about 70% of the alkoxide is adsorbed. In some embodiments of the process for the recovery of an alkoxide, the eluting through the adsorbent is performed until at least about 80% of the alkoxide is adsorbed. In some embodiments of the process for the recovery of an alkoxide, the eluting through the adsorbent is performed until at least about 90% of the alkoxide is adsorbed. In some embodiments of the process for the recovery of an alkoxide, the eluting through the adsorbent is performed until at least about 95% of the alkoxide is adsorbed. In some embodiments of the process for the recovery of an alkoxide, the eluting through the adsorbent is performed until at least about 99% of the alkoxide is adsorbed.

In some embodiments of the process for the recovery of an alkoxide, the adsorbent is silica gel, a silicate derivative, $Al_2O_3$, polymeric alumina, zeolites, activated carbon, polysulfones, polysulfates, polycarboxylates, or any combinations thereof.

In some embodiments of the process for the recovery of an alkoxide, the silicate derivative is sepiolite, palygorskite, hydrotalcite, kaolinite, or diopside. In some embodiments of the process for the recovery of an alkoxide, the adsorbent is silica gel with pore size between about 10 μm and about 800 μm. In some embodiments of the process for the recovery of an alkoxide, the adsorbent is silica gel with specific surface area between about 20 $m^2/g$ and about 1000 $m^2/g$. In some embodiments of the process for the recovery of an alkoxide, the adsorbent is basic alumina, neutral alumina, or acidic alumina. In some embodiments of the process for the recovery of an alkoxide, the adsorbent is a mixture of alumina and silica gel. In some embodiments of the process for the recovery of an alkoxide, the adsorbent is a mixture of zeolites and silica gel.

Step (ii): Wash Cycle

In some embodiments of the process for the recovery of an alkoxide, the wash cycle comprises washing the adsorbent with a wash solvent. In some embodiments of the process for the recovery of an alkoxide, the wash cycle comprises washing the surface of the adsorbent with a wash solvent. In some embodiments of the process for the recovery of an alkoxide, the wash cycle comprises washing the adsorbent with a wash solvent, thereby eliminating ester salts, pigments, and dyes adsorbed during the adsorption cycle. In some embodiments of the process for the recovery of an alkoxide, the ester salts, pigments, and dyes adsorbed during the adsorption cycle are adsorbed on the surface of the adsorbent. In some embodiments of the process for the recovery of an alkoxide, the ester salts are monomethyl terephthalate or dimethyl terephthalate salts.

In some embodiments of the process for the recovery of an alkoxide, the wash cycle is co-current or counter current. In some embodiments of the process for the recovery of an alkoxide, the wash cycle is counter current. In some embodiments of the process for the recovery of an alkoxide, the wash cycle is co-current.

In some embodiments of the process for the recovery of an alkoxide, the washing is performed 1 to 20 times. In some embodiments of the process for the recovery of an alkoxide, the washing is performed 1 to 15 times. In some embodiments of the process for the recovery of an alkoxide, the washing is performed 1 to 10 times. In some embodiments of the process for the recovery of an alkoxide, the washing is performed 1 to 5 times. In some embodiments of the process for the recovery of an alkoxide, the washing is performed 1 to 3 times. In some embodiments of the process for the recovery of an alkoxide, the washing is performed 20 times, 19 times, 18 times, 17 times, 16 times, 15 times, 14 times, 13 times, 12 times, 11 times, 10 times, 9 times, 8 times, 7 times, 6 times, 5 times, 4 times, 3 times, 2 times, or once.

In some embodiments of the process for the recovery of an alkoxide, the washing is performed until at most between about 1% and about 30% of the alkoxide is desorbed from the adsorbent. In some embodiments of the process for the recovery of an alkoxide, the washing is performed until at most between about 1% and about 20% of the alkoxide is desorbed from the adsorbent. In some embodiments of the process for the recovery of an alkoxide, the washing is performed until at most between about 1% and about 10% of the alkoxide is desorbed from the adsorbent. In some embodiments of the process for the recovery of an alkoxide, the washing is performed until at most between about 1% and about 5% of the alkoxide is desorbed from the adsorbent. In some embodiments of the process for the recovery of an alkoxide, the washing is performed until at most about 30% of the alkoxide is desorbed from the adsorbent. In some embodiments of the process for the recovery of an alkoxide, the washing is performed until at most about 25% of the alkoxide is desorbed from the adsorbent. In some embodiments of the process for the recovery of an alkoxide, the washing is performed until at most about 20% of the alkoxide is desorbed from the adsorbent. In some embodiments of the process for the recovery of an alkoxide, the washing is performed until at most about 15% of the alkoxide is desorbed from the adsorbent. In some embodiments of the process for the recovery of an alkoxide, the washing is performed until at most about 10% of the alkoxide is desorbed from the adsorbent. In some embodiments of the process for the recovery of an alkoxide, the washing is performed until at most about 5% of the alkoxide is desorbed from the adsorbent. In some embodiments of the process for the recovery of an alkoxide, the washing is performed until at most about 1% of the alkoxide is desorbed from the adsorbent.

In some embodiments of the process for the recovery of an alkoxide, the wash solvent is a polar protic solvent. In some embodiments of the process for the recovery of an alkoxide, the wash solvent is a polar aprotic solvent. In some embodiments of the process for the recovery of an alkoxide, the wash solvent is an apolar aprotic solvent. In some embodiments of the process for the recovery of an alkoxide, the wash solvent is an alcoholic solvent. In some embodiments of the process for the recovery of an alkoxide, the wash solvent is methanol, ethanol, propanol, butanol, or any combinations thereof. In some embodiments of the process for the recovery of an alkoxide, the wash solvent is a mixture of an alcoholic solvent and a polar solvent. In some embodiments of the process for the recovery of an alkoxide, the wash solvent is a mixture of an alcoholic solvent and an apolar solvent. In some embodiments of the process for the recovery of an alkoxide, the wash solvent is methanol. In some embodiments of the process for the recovery of an alkoxide, the wash solvent is methanol and cyclohexane. In some embodiments of the process for the recovery of an alkoxide, the wash solvent is methanol and acetonitrile. In some embodiments of the process for the recovery of an alkoxide, the wash solvent is cyclohexane/mono ethylene glycol/methanol.

Step (iii): Desorption Cycle

In some embodiments of the process for the recovery of an alkoxide, the desorption cycle comprises washing the adsorbent with a desorption solvent, thereby obtaining a mixture comprising the alkoxide and the desorption solvent.

In some embodiments of the process for the recovery of an alkoxide, the washing to obtain the mixture comprising the alkoxide and the desorption solvent is performed 1 to 20 times. In some embodiments of the process for the recovery of an alkoxide, the washing to obtain the mixture comprising the alkoxide and the desorption solvent is performed 1 to 15 times. In some embodiments of the process for the recovery of an alkoxide, the washing to obtain the mixture comprising the alkoxide and the desorption solvent is performed 1 to 10 times. In some embodiments of the process for the recovery of an alkoxide, the washing to obtain the mixture comprising the alkoxide and the desorption solvent is performed 1 to 5 times. In some embodiments of the process for the recovery of an alkoxide, the washing to obtain the mixture comprising the alkoxide and the desorption solvent is performed 1 to 3 times. In some embodiments of the process for the recovery of an alkoxide, the washing to obtain the mixture comprising the alkoxide and the desorption solvent is performed 20 times, 19 times, 18 times, 17 times, 16 times, 15 times, 14 times, 13 times, 12 times, 11 times, 10 times, 9 times, 8 times, 7 times, 6 times, 5 times, 4 times, 3 times, 2 times, or once.

In some embodiments of the process for the recovery of an alkoxide, the washing to obtain the mixture comprising the alkoxide and the desorption solvent is performed until at least between about 30% and about 99% of the alkoxide is desorbed from the adsorbent. In some embodiments of the process for the recovery of an alkoxide, the washing to obtain the mixture comprising the alkoxide and the desorption solvent is performed until at least between about 50% and about 99% of the alkoxide is desorbed from the adsorbent. In some embodiments of the process for the recovery of an alkoxide, the washing to obtain the mixture comprising the alkoxide and the desorption solvent is performed until at least between about 90% and about 99% of the alkoxide is desorbed from the adsorbent. In some embodiments of the process for the recovery of an alkoxide, the washing to obtain the mixture comprising the alkoxide and the desorption solvent is performed until at least about 30% of the alkoxide is desorbed from the adsorbent. In some embodiments of the process for the recovery of an alkoxide, the washing to obtain the mixture comprising the alkoxide and the desorption solvent is performed until at least about 40% of the alkoxide is desorbed from the adsorbent. In some embodiments of the process for the recovery of an alkoxide, the washing to obtain the mixture comprising the alkoxide and the desorption solvent is performed until at least about 50% of the alkoxide is desorbed from the adsorbent. In some embodiments of the process for the recovery of an alkoxide, the washing to obtain the mixture comprising the alkoxide and the desorption solvent is performed until at least about 60% of the alkoxide is desorbed from the adsorbent. In some embodiments of the process for the recovery of an alkoxide, the washing to obtain the mixture comprising the alkoxide and the desorption solvent is performed until at least about 70% of the alkoxide is desorbed from the adsorbent. In some embodiments of the process for the recovery of an alkoxide, the washing to obtain the mixture comprising the alkoxide and the desorption solvent is performed until at least about 80% of the alkoxide is desorbed from the adsorbent. In some embodiments of the process for the recovery of an alkoxide, the washing to obtain the mixture comprising the alkoxide and the desorption solvent is performed until at least about 90% of the alkoxide is desorbed from the adsorbent. In some embodiments of the process for the recovery of an alkoxide, the washing to obtain the mixture comprising the alkoxide and the desorption solvent is performed until at least about 95% of the alkoxide is desorbed from the adsorbent. In some embodiments of the process for the recovery of an alkoxide, the washing to obtain the mixture comprising the alkoxide and the desorption solvent is performed until at least about 99% of the alkoxide is desorbed from the adsorbent.

In some embodiments of the process for the recovery of an alkoxide, the washing to obtain the mixture comprising the alkoxide and the desorption solvent is performed at room temperature. In some embodiments of the process for the recovery of an alkoxide, the washing to obtain the mixture comprising the alkoxide and the desorption solvent is performed at elevated temperature. In some embodiments of the process for the recovery of an alkoxide, the washing to obtain the mixture comprising the alkoxide and the desorption solvent is performed at about 30° C., about 35° C., about 40° C., about 45° C., about 50° C., about 55° C., about 60° C., about 65° C., or about 70° C.

In some embodiments of the process for the recovery of an alkoxide, the desorption solvent is a polar protic solvent. In some embodiments of the process for the recovery of an alkoxide, the desorption solvent is a polar aprotic solvent. In some embodiments of the process for the recovery of an alkoxide, the desorption solvent is an apolar aprotic solvent. In some embodiments of the process for the recovery of an alkoxide, the desorption solvent is an alcoholic solvent. In some embodiments of the process for the recovery of an alkoxide, the desorption solvent is methanol, ethanol, propanol, butanol, or any combinations thereof. In some embodiments of the process for the recovery of an alkoxide, the desorption solvent is a mixture of an alcoholic solvent and a polar solvent. In some embodiments of the process for the recovery of an alkoxide, the desorption solvent is a mixture of an alcoholic solvent and an apolar solvent. In some embodiments of the process for the recovery of an alkoxide, the desorption solvent is methanol. In some embodiments of the process for the recovery of an alkoxide, the desorption solvent is methanol and cyclohexane. In some embodiments of the process for the recovery of an alkoxide, the desorption solvent is methanol and acetonitrile. In some embodiments of the process for the recovery of an alkoxide, the desorption solvent is cyclohexane/mono ethylene glycol/methanol.

In some embodiments of the process for the recovery of an alkoxide, a portion of the desorption solvent in the mixture comprising the alkoxide and the desorption solvent is subsequently removed. In some embodiments of the process for the recovery of an alkoxide, a portion of the desorption solvent is removed under vacuum. In some embodiments of the process for the recovery of an alkoxide, a portion of the desorption solvent is removed under pressure.

In some embodiments of the process for the recovery of an alkoxide, the final concentration of the alkoxide in the desorption solvent is between about 0.1 wt-% to about 100 wt-%. In some embodiments of the process for the recovery of an alkoxide, the final concentration of the alkoxide in the desorption solvent is between about 0.1 wt-% to about 90 wt-%. In some embodiments of the process for the recovery of an alkoxide, the final concentration of the alkoxide in the desorption solvent is between about 0.1 wt-% to about 80 wt-%. In some embodiments of the process for the recovery of an alkoxide, the final concentration of the alkoxide in the desorption solvent is between about 0.1 wt-% to about 70 wt-%. In some embodiments of the process for the recovery of an alkoxide, the final concentration of the alkoxide in the desorption solvent is between about 0.1 wt-% to about 60 wt-%. In some embodiments of the process for the recovery of an alkoxide, the final concentration of the alkoxide in the desorption solvent is between about 0.1 wt-% to about 50 wt-%. In some embodiments of the process for the recovery of an alkoxide, the final concentration of the alkoxide in the desorption solvent is between about 0.1 wt-% to about 40 wt-%. In some embodiments of the process for the recovery of an alkoxide, the final concentration of the alkoxide in the desorption solvent is between about 0.1 wt-% to about 30 wt-%. In some embodiments of the process for the recovery of an alkoxide, the final concentration of the alkoxide in the desorption solvent is between about 0.1 wt-% to about 20 wt-%. In some embodiments of the process for the recovery of an alkoxide, the final concentration of the alkoxide in the desorption solvent is between about 0.1 wt-% to about 10 wt-%.

In some embodiments of the process for the recovery of an alkoxide, the alkoxide in the desorption solvent is re-used in a process of depolymerizing a polyester to form an organic diacid and a diol. In some embodiments of the process for the recovery of an alkoxide, the alkoxide in the desorption solvent is re-used in a process of depolymerizing a polyester to form a diester and a diol. In some embodiments of the process for the recovery of an alkoxide, the diol formed is mono ethylene glycol (MEG) (or ethylene glycol). In some embodiments of the process for the recovery of an alkoxide, the diol formed is propylene glycol. In some embodiments of the process for the recovery of an alkoxide, the diol formed is butylene glycol. In some embodiments of the process for the recovery of an alkoxide, the diacid formed is terephthalic acid. In some embodiments of the process for the recovery of an alkoxide, the diester formed is dimethyl terephthalate (DMT).

In some embodiments of the process for the recovery of an alkoxide, the alkoxide in the desorption solvent is re-used in a process of depolymerizing polyethylene terephthalate (PET) to form a terephthalate and/or an isophthalate, and mono ethylene glycol (MEG).

In some embodiments of the process for the recovery of an alkoxide, the alkoxide is an alkali metal alkoxide, an alkaline earth metal alkoxide, a metal alkoxide, an ammonium alkoxide, or any combinations thereof. In some embodiments of the process for the recovery of an alkoxide, the alkoxide is sodium methoxide, sodium glycoxide, potassium ethoxide, aluminum tri-n-propoxide, tetrabutylammonium methoxide, or any combinations thereof. In some embodiments of the process for the recovery of an alkoxide, the alkoxide is sodium methoxide. In some embodiments of the process for the recovery of an alkoxide, the alkoxide is sodium glycoxide.

In some embodiments of the process for the recovery of an alkoxide, the process further comprises (iv) a regeneration cycle.

In some embodiments of the process for the recovery of an alkoxide, the process comprises:
 (i) an adsorption cycle;
 (ii) a wash cycle;
 (iii) a desorption cycle; and
 (iv) a regeneration cycle.

Step (iv): Regeneration Cycle

In some embodiments of the process for the recovery of an alkoxide, the regeneration cycle comprises washing the adsorbent with an acid, thereby regenerating the adsorbent.

In some embodiments of the process for the recovery of an alkoxide, the washing is performed 1 to 20 times. In some embodiments of the process for the recovery of an alkoxide, the washing is performed 1 to 15 times. In some embodiments of the process for the recovery of an alkoxide, the washing is performed 1 to 10 times. In some embodiments of the process for the recovery of an alkoxide, the washing is performed 1 to 5 times. In some embodiments of the process for the recovery of an alkoxide, the washing is performed 1 to 3 times. In some embodiments of the process for the recovery of an alkoxide, the washing is performed 20 times, 19 times, 18 times, 17 times, 16 times, 15 times, 14 times, 13 times, 12 times, 11 times, 10 times, 9 times, 8 times, 7 times, 6 times, 5 times, 4 times, 3 times, 2 times, or once.

In some embodiments of the process for the recovery of an alkoxide, the acid is acetic acid, formic acid, hydrochloric acid, sulfuric acid, phosphoric acid, or any combinations thereof. In some embodiments of the process for the recovery of an alkoxide, the acid is acetic acid. In some embodiments of the process for the recovery of an alkoxide, the acid is formic acid.

In some embodiments of the process for the recovery of an alkoxide, one regeneration cycle is performed for every 5 to 100 (i) adsorption cycle/(ii) wash cycle/(iii) desorption cycle. In some embodiments of the process for the recovery of an alkoxide, one regeneration cycle is performed for every 25 to 100 (i) adsorption cycle/(ii) wash cycle/(iii) desorption cycle. In some embodiments of the process for the recovery of an alkoxide, one regeneration cycle is performed for every 50 to 100 (i) adsorption cycle/(ii) wash cycle/(iii) desorption cycle. In some embodiments of the process for the recovery of an alkoxide, one regeneration cycle is performed for every 100 (i) adsorption cycle/(ii) wash cycle/(iii) desorption cycle. In some embodiments of the process for the recovery of an alkoxide, one regeneration cycle is performed for every 50 (i) adsorption cycle/(ii) wash cycle/(iii) desorption cycle. In some embodiments of the process for the recovery of an alkoxide, one regeneration cycle is performed for every 40 (i) adsorption cycle/(ii) wash cycle/(iii) desorption cycle. In some embodiments of the process for the recovery of an alkoxide, one regeneration cycle is performed for every 30 (i) adsorption cycle/(ii) wash cycle/(iii) desorption cycle. In some embodiments of the process for the recovery of an alkoxide, one regeneration cycle is performed for every 20 (i) adsorption cycle/(ii) wash cycle/(iii) desorption cycle. In some embodiments of the process for the recovery of an alkoxide, one regeneration cycle is performed for every 10 (i) adsorption cycle/(ii) wash cycle/(iii) desorption cycle. In some embodiments of the process for the recovery of an alkoxide, one regeneration cycle is performed for every 5 (i) adsorption cycle/(ii) wash cycle/(iii) desorption cycle.

Also disclosed herein is a process for purifying a diol mother liquor; the process comprising:
 (i) an adsorption cycle;
 (ii) a wash cycle; and
 (iii) a desorption cycle.

In some embodiments of the process for purifying a diol mother liquor, the diol is mono ethylene glycol (MEG). In some embodiments of the process for purifying a diol mother liquor, the diol is propylene glycol. In some embodiments of the process for purifying a diol mother liquor, the diol is butylene glycol. In some embodiments of the process for purifying a diol mother liquor, the diol is 1,4-cyclohexanedimethanol (1,4-bis(hydroxymethyl)cyclohexane). In some embodiments of the process for purifying a diol mother liquor, the diol is 2,2,4,4-tetramethyl-1,3-cyclobutanediol.

In some embodiments of the process for purifying a diol mother liquor, the adsorption cycle, wash cycle, and desorption cycle are performed sequentially. In some embodiments of the process for purifying a diol mother liquor, the adsorption cycle and/or wash cycle and/or desorption cycle are performed continuously.

In some embodiments of the process for purifying a diol mother liquor, the diol mother liquor is obtained from a process of depolymerizing a polyester to form an organic diacid and a diol. In some embodiments of the process for purifying a diol mother liquor, the diol mother liquor is obtained from a process of depolymerizing a polyester to form a diester and a diol. In some embodiments of the process for purifying a diol mother liquor, the diol is mono ethylene glycol (MEG) (or ethylene glycol). In some embodiments of the process for purifying a diol mother liquor, the diol is propylene glycol. In some embodiments of the process for purifying a diol mother liquor, the diol is butylene glycol. In some embodiments of the process for purifying a diol mother liquor, the diol is 1,4-cyclohexanedimethanol (1,4-bis(hydroxymethyl)cyclohexane). In some embodiments of the process for purifying a diol mother liquor, the diol is 2,2,4,4-tetramethyl-1,3-cyclobutanediol. In some embodiments of the process for purifying a diol mother liquor, the diacid is terephthalic acid. In some embodiments of the process for purifying a diol mother liquor, the diacid is isophthalic acid. In some embodiments of the process for purifying a diol mother liquor, the diester is dimethyl terephthalate (DMT). In some embodiments of the process for purifying a diol mother liquor, the diester is dimethyl isophthalate (DMI). In some embodiments of the process for purifying a diol mother liquor, the polyester is selected from polyethylene terephthalate (PET), poly(ethylene glycol-co-1,4-cyclohexanedimethanol terephthalate) (PETG), polyglycolide or polyglycolic acid (PGA), polylactic acid (PLA), polycaprolactone (PCL), polyhydroxybutyrate (PHB), polyethylene adipate (PEA), polybutylene succinate (PBS), poly(3-hydroxybutyrate-co-3-hydroxyvalerate) (PHBV), polybutylene terephthalate (PBT), polytrimethylene terephthalate (PTT), polyethylene naphthalate (PEN), Vectran®, cutin, and any combinations thereof. In some embodiments of the process for purifying a diol mother liquor, the polyester is polyethylene terephthalate (PET). In some embodiments of the process for purifying a diol mother liquor, the polyester is poly(ethylene glycol-co-1,4-cyclohexanedimethanol terephthalate) (PETG).

In some embodiments of the process for purifying a diol mother liquor, the diol mother liquor is obtained from a process of depolymerizing polyethylene terephthalate (PET) to form a terephthalate and/or an isophthalate, and mono ethylene glycol (MEG).

In some embodiments of the process for purifying a diol mother liquor, the terephthalate is dimethyl terephthalate. In some embodiments of the process for purifying a diol mother liquor, the isophthalate is dimethyl isophthalate.

In some embodiments of the process for purifying a diol mother liquor, the diol mother liquor further comprises an alkoxide. In some embodiments of the process for purifying a diol mother liquor, the alkoxide is an alkali metal alkoxide, an alkaline earth metal alkoxide, a metal alkoxide, an ammonium alkoxide, or any combinations thereof. In some embodiments of the process for purifying a diol mother liquor, the alkoxide is sodium methoxide, sodium glycoxide, potassium ethoxide, aluminum tri-n-propoxide, tetrabutylammonium methoxide, or any combinations thereof. In some embodiments of the process for purifying a diol mother liquor, the alkoxide is sodium methoxide. In some embodiments of the process for purifying a diol mother liquor, the alkoxide is sodium glycoxide.

Step (i): Adsorption Cycle

In some embodiments of the process for purifying a diol mother liquor, the adsorption cycle comprises contacting the diol mother liquor through an adsorbent, thereby adsorbing the alkoxide. In some embodiments of the process for purifying a diol mother liquor, the adsorption cycle comprises eluting the diol mother liquor through an adsorbent, thereby adsorbing the alkoxide.

In some embodiments of the process for purifying a diol mother liquor, the eluting through the adsorbent is performed 1 to 20 times. In some embodiments of the process for purifying a diol mother liquor, the eluting through the adsorbent is performed 1 to 15 times. In some embodiments of the process for purifying a diol mother liquor, the eluting through the adsorbent is performed 1 to 10 times. In some embodiments of the process for purifying a diol mother liquor, the eluting through the adsorbent is performed 1 to 5 times. In some embodiments of the process for purifying a diol mother liquor, the eluting through the adsorbent is performed 1 to 3 times. In some embodiments of the process for purifying a diol mother liquor, the eluting through the adsorbent is performed 20 times, 19 times, 18 times, 17 times, 16 times, 15 times, 14 times, 13 times, 12 times, 11 times, 10 times, 9 times, 8 times, 7 times, 6 times, 5 times, 4 times, 3 times, 2 times, or once.

In some embodiments of the process for purifying a diol mother liquor, the eluting through the adsorbent is performed until at least between about 30% and about 99% of the alkoxide is adsorbed. In some embodiments of the process for purifying a diol mother liquor, the eluting through the adsorbent is performed until at least between about 50% and about 99% of the alkoxide is adsorbed. In some embodiments of the process for purifying a diol mother liquor, the eluting through the adsorbent is performed until at least between about 80% and about 99% of the alkoxide is adsorbed. In some embodiments of the process for purifying a diol mother liquor, the eluting through the adsorbent is performed until at least between about 90% and about 99% of the alkoxide is adsorbed. In some embodiments of the process for purifying a diol mother liquor, the eluting through the adsorbent is performed until at least about 30% of the alkoxide is adsorbed. In some embodiments of the process for purifying a diol mother liquor, the eluting through the adsorbent is performed until at least about 40% of the alkoxide is adsorbed. In some embodiments of the process for purifying a diol mother liquor, the eluting through the adsorbent is performed until at least about 50% of the alkoxide is adsorbed. In some embodiments of the process for purifying a diol mother liquor, the eluting through the adsorbent is performed until at least about 60% of the alkoxide is adsorbed. In some embodiments of the process for purifying a diol mother liquor, the eluting through the adsorbent is performed until at least about 70% of the alkoxide is adsorbed. In some embodiments of the process for purifying a diol mother liquor, the eluting through the adsorbent is performed until at least about 80% of the alkoxide is adsorbed. In some embodiments of the process for purifying a diol mother liquor, the eluting through the adsorbent is performed until at least about 90% of the alkoxide is adsorbed. In some embodiments of the process for purifying a diol mother liquor, the eluting through the adsorbent is performed until at least about 95% of the alkoxide is adsorbed. In some embodiments of the process for purifying a diol mother liquor, the eluting through the adsorbent is performed until at least about 99% of the alkoxide is adsorbed.

In some embodiments of the process for purifying a diol mother liquor, the adsorbent is silica gel, a silicate derivative, $Al_2O_3$, polymeric alumina, zeolites, activated carbon, polysulfones, polysulfates, polycarboxylates, or any combinations thereof. In some embodiments of the process for purifying a diol mother liquor, the silicate derivative is sepiolite, palygorskite, hydrotalcite, kaolinite, or diopside. In some embodiments of the process for purifying a diol mother liquor, the adsorbent is silica gel with pore size between about 10 μm and about 800 μm. In some embodiments of the process for purifying a diol mother liquor, the adsorbent is silica gel with specific surface area between about 20 $m^2$/g and about 1000 $m^2$/g. In some embodiments of the process for purifying a diol mother liquor, the adsorbent is basic alumina, neutral alumina, or acidic alumina. In some embodiments of the process for purifying a diol mother liquor, the adsorbent is a mixture of alumina and silica gel. In some embodiments of the process for purifying a diol mother liquor, the adsorbent is a mixture of zeolites and silica gel.

Step (ii): Wash Cycle

In some embodiments of the process for purifying a diol mother liquor, the wash cycle comprises washing the adsorbent with a wash solvent. In some embodiments of the process for purifying a diol mother liquor, the wash cycle comprises washing the surface of the adsorbent with a wash solvent. In some embodiments of the process for purifying a diol mother liquor, the wash cycle comprises washing the adsorbent with a wash solvent, thereby eliminating ester salts, pigments, and dyes adsorbed during the adsorption cycle. In some embodiments of the process for purifying a diol mother liquor, the ester salts, pigments, and dyes adsorbed during the adsorption cycle are adsorbed on the surface of the adsorbent. In some embodiments of the process for purifying a diol mother liquor, the ester salts are monomethyl terephthalate or dimethyl terephthalate salts.

In some embodiments of the process for purifying a diol mother liquor, the wash cycle is co-current or counter current. In some embodiments of the process for purifying a diol mother liquor, the wash cycle is counter current. In some embodiments of the process for purifying a diol mother liquor, the wash cycle is co-current.

In some embodiments of the process for purifying a diol mother liquor, the washing is performed 1 to 20 times. In some embodiments of the process for purifying a diol mother liquor, the washing is performed 1 to 15 times. In some embodiments of the process for purifying a diol mother liquor, the washing is performed 1 to 10 times. In some embodiments of the process for purifying a diol mother liquor, the washing is performed 1 to 5 times. In some embodiments of the process for purifying a diol mother liquor, the washing is performed 1 to 3 times. In some embodiments of the process for purifying a diol mother liquor, the washing is performed 20 times, 19 times, 18 times, 17 times, 16 times, 15 times, 14 times, 13 times, 12 times, 11 times, 10 times, 9 times, 8 times, 7 times, 6 times, 5 times, 4 times, 3 times, 2 times, or once.

In some embodiments of the process for purifying a diol mother liquor, the washing is performed until at most between about 1% and about 30% of the alkoxide is desorbed from the adsorbent. In some embodiments of the process for purifying a diol mother liquor, the washing is performed until at most between about 1% and about 20% of the alkoxide is desorbed from the adsorbent. In some embodiments of the process for purifying a diol mother liquor, the washing is performed until at most between about 1% and about 10% of the alkoxide is desorbed from the adsorbent. In some embodiments of the process for purifying a diol mother liquor, the washing is performed until at most between about 1% and about 5% of the alkoxide is desorbed from the adsorbent. In some embodiments of the process for purifying a diol mother liquor, the washing is performed until at most about 30% of the alkoxide is desorbed from the adsorbent. In some embodiments of the process for purifying a diol mother liquor, the washing is performed until at most about 25% of the alkoxide is desorbed from the adsorbent. In some embodiments of the process for purifying a diol mother liquor, the washing is performed until at most about 20% of the alkoxide is desorbed from the adsorbent. In some embodiments of the process for purifying a diol mother liquor, the washing is performed until at most about 15% of the alkoxide is desorbed from the adsorbent. In some embodiments of the process for purifying a diol mother liquor, the washing is performed until at most about 10% of the alkoxide is desorbed from the adsorbent. In some embodiments of the process for purifying a diol mother liquor, the washing is performed until at most about 5% of the alkoxide is desorbed from the adsorbent. In some embodiments of the process for purifying a diol mother liquor, the washing is performed until at most about 1% of the alkoxide is desorbed from the adsorbent.

In some embodiments of the process for purifying a diol mother liquor, the wash solvent is a polar protic solvent. In some embodiments of the process for purifying a diol mother liquor, the wash solvent is a polar aprotic solvent. In some embodiments of the process for purifying a diol mother liquor, the wash solvent is an apolar aprotic solvent. In some embodiments of the process for purifying a diol mother liquor, the wash solvent is an alcoholic solvent. In some embodiments of the process for purifying a diol mother liquor, the wash solvent is methanol, ethanol, propanol, butanol, or any combinations thereof. In some embodiments of the process for purifying a diol mother liquor, the wash solvent is a mixture of an alcoholic solvent and a polar solvent. In some embodiments of the process for purifying a diol mother liquor, the wash solvent is a mixture of an alcoholic solvent and an apolar solvent. In some embodiments of the process for purifying a diol mother liquor, the wash solvent is methanol. In some embodiments of the process for purifying a diol mother liquor, the wash solvent is methanol and cyclohexane. In some embodiments of the process for purifying a diol mother liquor, the wash solvent is methanol and acetonitrile. In some embodiments of the process for purifying a diol mother liquor, the wash solvent is cyclohexane/mono ethylene glycol/methanol.

Step (iii): Desorption Cycle

In some embodiments of the process for purifying a diol mother liquor, the desorption cycle comprises washing the adsorbent with a desorption solvent, thereby obtaining a mixture comprising the alkoxide and the desorption solvent.

In some embodiments of the process for purifying a diol mother liquor, the washing to obtain the mixture comprising the alkoxide and the desorption solvent is performed 1 to 20 times. In some embodiments of the process for purifying a diol mother liquor, the washing to obtain the mixture comprising the alkoxide and the desorption solvent is performed 1 to 15 times. In some embodiments of the process for purifying a diol mother liquor, the washing to obtain the mixture comprising the alkoxide and the desorption solvent is performed 1 to 10 times. In some embodiments of the process for purifying a diol mother liquor, the washing to obtain the mixture comprising the alkoxide and the desorption solvent is performed 1 to 5 times. In some embodiments of the process for purifying a diol mother liquor, the washing to obtain the mixture comprising the alkoxide and the desorption solvent is performed 1 to 3 times. In some embodiments of the process for purifying a diol mother liquor, the washing to obtain the mixture comprising the alkoxide and the desorption solvent is performed 20 times, 19 times, 18 times, 17 times, 16 times, 15 times, 14 times, 13 times, 12 times, 11 times, 10 times, 9 times, 8 times, 7 times, 6 times, 5 times, 4 times, 3 times, 2 times, or once.

In some embodiments of the process for purifying a diol mother liquor, the washing to obtain the mixture comprising the alkoxide and the desorption solvent is performed until at least between about 30% and about 99% of the alkoxide is desorbed from the adsorbent. In some embodiments of the process for purifying a diol mother liquor, the washing to obtain the mixture comprising the alkoxide and the desorption solvent is performed until at least between about 50% and about 99% of the alkoxide is desorbed from the adsorbent. In some embodiments of the process for purifying a diol mother liquor, the washing to obtain the mixture comprising the alkoxide and the desorption solvent is performed until at least between about 90% and about 99% of the alkoxide is desorbed from the adsorbent. In some embodiments of the process for purifying a diol mother liquor, the washing to obtain the mixture comprising the alkoxide and the desorption solvent is performed until at least about 30% of the alkoxide is desorbed from the adsorbent. In some embodiments of the process for purifying a diol mother liquor, the washing to obtain the mixture comprising the alkoxide and the desorption solvent is performed until at least about 40% of the alkoxide is desorbed from the adsorbent. In some embodiments of the process for purifying a diol mother liquor, the washing to obtain the mixture comprising the alkoxide and the desorption solvent is performed until at least about 50% of the alkoxide is desorbed from the adsorbent. In some embodiments of the process for purifying a diol mother liquor, the washing to obtain the mixture comprising the alkoxide and the desorption solvent is performed until at least about 60% of the alkoxide is desorbed from the adsorbent. In some embodiments of the process for purifying a diol mother liquor, the washing to obtain the mixture comprising the alkoxide and the desorption solvent is performed until at least about 70% of the alkoxide is desorbed from the adsorbent. In some embodiments of the process for purifying a diol mother liquor, the washing to obtain the mixture comprising the alkoxide and the desorption solvent is performed until at least about 80% of the alkoxide is desorbed from the adsorbent. In some embodiments of the process for purifying a diol mother liquor, the washing to obtain the mixture comprising the alkoxide and the desorption solvent is performed until at least about 90% of the alkoxide is desorbed from the adsorbent. In some embodiments of the process for purifying a diol mother liquor, the washing to obtain the mixture comprising the alkoxide and the desorption solvent is performed until at least about 95% of the alkoxide is desorbed from the adsorbent. In some embodiments of the process for purifying a diol mother liquor, the washing to obtain the mixture comprising the alkoxide and the desorption solvent is performed until at least about 99% of the alkoxide is desorbed from the adsorbent.

In some embodiments of the process for purifying a diol mother liquor, the washing to obtain the mixture comprising the alkoxide and the desorption solvent is performed at room temperature. In some embodiments of the process for purifying a diol mother liquor, the washing to obtain the mixture comprising the alkoxide and the desorption solvent is performed at elevated temperature. In some embodiments of the process for purifying a diol mother liquor, the washing to obtain the mixture comprising the alkoxide and the desorption solvent is performed at about 30° C., about 35° C., about 40° C., about 45° C., about 50° C., about 55° C., about 60° C., about 65° C., or about 70° C.

In some embodiments of the process for purifying a diol mother liquor, the desorption solvent is a polar protic solvent. In some embodiments of the process for purifying a diol mother liquor, the desorption solvent is a polar aprotic solvent. In some embodiments of the process for purifying a diol mother liquor, the desorption solvent is an apolar aprotic solvent. In some embodiments of the process for purifying a diol mother liquor, the desorption solvent is an alcoholic solvent. In some embodiments of the process for purifying a diol mother liquor, the desorption solvent is methanol, ethanol, propanol, butanol, or any combinations thereof. In some embodiments of the process for purifying a diol mother liquor, the desorption solvent is a mixture of an alcoholic solvent and a polar solvent. In some embodiments of the process for purifying a diol mother liquor, the desorption solvent is a mixture of an alcoholic solvent and an apolar solvent. In some embodiments of the process for purifying a diol mother liquor, the desorption solvent is methanol. In some embodiments of the process for purifying a diol mother liquor, the desorption solvent is methanol and cyclohexane. In some embodiments of the process for purifying a diol mother liquor, the desorption solvent is methanol and acetonitrile. In some embodiments of the process for purifying a diol mother liquor, the desorption solvent is cyclohexane/mono ethylene glycol/methanol.

In some embodiments of the process for purifying a diol mother liquor, a portion of the desorption solvent in the mixture comprising the alkoxide and the desorption solvent is subsequently removed. In some embodiments of the process for purifying a diol mother liquor, a portion of the desorption solvent is removed under vacuum. In some embodiments of the process for purifying a diol mother liquor, a portion of the desorption solvent is removed under pressure.

In some embodiments of the process for purifying a diol mother liquor, the final concentration of the alkoxide in the desorption solvent is between about 0.1 wt-% to about 100 wt-%. In some embodiments of the process for purifying a diol mother liquor, the final concentration of the alkoxide in the desorption solvent is between about 0.1 wt-% to about 90 wt-%. In some embodiments of the process for purifying a diol mother liquor, the final concentration of the alkoxide in the desorption solvent is between about 0.1 wt-% to about 80 wt-%. In some embodiments of the process for purifying a diol mother liquor, the final concentration of the alkoxide in the desorption solvent is between about 0.1 wt-% to about 70 wt-%. In some embodiments of the process for purifying a diol mother liquor, the final concentration of the alkoxide in the desorption solvent is between about 0.1 wt-% to about 60 wt-%. In some embodiments of the process for purifying a diol mother liquor, the final concentration of the alkoxide in the desorption solvent is between about 0.1 wt-% to about 50 wt-%. In some embodiments of the process for purifying a diol mother liquor, the final concentration of the alkoxide in the desorption solvent is between about 0.1 wt-% to about 40 wt-%. In some embodiments of the process for purifying a diol mother liquor, the final concentration of the alkoxide in the desorption solvent is between about 0.1 wt-% to about 30 wt-%. In some embodiments of the process for purifying a diol mother liquor, the final concentration of the alkoxide in the desorption solvent is between about 0.1 wt-% to about 20 wt-%. In some embodiments of the process for purifying a diol mother liquor, the final concentration of the alkoxide in the desorption solvent is between about 0.1 wt-% to about 10 wt-%.

In some embodiments of the process for purifying a diol mother liquor, the alkoxide in the desorption solvent is re-used in a process of depolymerizing a polyester to form an organic diacid and a diol. In some embodiments of the process for purifying a diol mother liquor, the alkoxide in the desorption solvent is re-used in a process of depolymerizing a polyester to form a diester and a diol. In some embodiments of the process for purifying a diol mother liquor, the diol formed is mono ethylene glycol (MEG) (or ethylene glycol). In some embodiments of the process for purifying a diol mother liquor, the diol formed is propylene glycol. In some embodiments of the process for purifying a diol mother liquor, the diol formed is butylene glycol. In some embodiments of the process for purifying a diol mother liquor, the diacid formed is terephthalic acid. In some embodiments of the process for purifying a diol mother liquor, the diester formed is dimethyl terephthalate (DMT).

In some embodiments of the process for purifying a diol mother liquor, the alkoxide in the desorption solvent is re-used in a process of depolymerizing polyethylene terephthalate (PET) to form a terephthalate and/or an isophthalate and mono ethylene glycol (MEG).

In some embodiments of the process for purifying a diol mother liquor, the alkoxide is an alkali metal alkoxide, an alkaline earth metal alkoxide, a metal alkoxide, an ammonium alkoxide, or any combinations thereof. In some embodiments of the process for purifying a diol mother liquor, the alkoxide is sodium methoxide, sodium glycoxide, potassium ethoxide, aluminum tri-n-propoxide, tetrabutylammonium methoxide, or any combinations thereof. In some embodiments of the process for purifying a diol mother liquor, the alkoxide is sodium methoxide. In some embodiments of the process for purifying a diol mother liquor, the alkoxide is sodium glycoxide.

In some embodiments of the process for purifying a diol mother liquor, the process further comprises (iv) a regeneration cycle.

In some embodiments of the process for purifying a diol mother liquor, the process comprises:
(i) an adsorption cycle;
(ii) a wash cycle;
(iii) a desorption cycle; and
(iv) a regeneration cycle.

Step (iv): Regeneration Cycle

In some embodiments of the process for purifying a diol mother liquor, the regeneration cycle comprises washing the adsorbent with an acid, thereby regenerating the adsorbent.

In some embodiments of the process for purifying a diol mother liquor, the washing is performed 1 to 20 times. In some embodiments of the process for purifying a diol mother liquor, the washing is performed 1 to 15 times. In some embodiments of the process for purifying a diol mother liquor, the washing is performed 1 to 10 times. In some embodiments of the process for purifying a diol mother liquor, the washing is performed 1 to 5 times. In some embodiments of the process for purifying a diol mother liquor, the washing is performed 1 to 3 times. In some embodiments of the process for purifying a diol mother liquor, the washing is performed 20 times, 19 times, 18 times, 17 times, 16 times, 15 times, 14 times, 13 times, 12 times, 11 times, 10 times, 9 times, 8 times, 7 times, 6 times, 5 times, 4 times, 3 times, 2 times, or once.

In some embodiments of the process for purifying a diol mother liquor, the acid is acetic acid, formic acid, hydrochloric acid, sulfuric acid, phosphoric acid, or any combinations thereof. In some embodiments of the process for purifying a diol mother liquor, the acid is acetic acid. In some embodiments of the process for purifying a diol mother liquor, the acid is formic acid.

In some embodiments of the process for purifying a diol mother liquor, one regeneration cycle is performed for every 5 to 100 (i) adsorption cycle/(ii) wash cycle/(iii) desorption cycle. In some embodiments of the process for purifying a diol mother liquor, one regeneration cycle is performed for every 25 to 100 (i) adsorption cycle/(ii) wash cycle/(iii) desorption cycle. In some embodiments of the process for purifying a diol mother liquor, one regeneration cycle is performed for every 50 to 100 (i) adsorption cycle/(ii) wash cycle/(iii) desorption cycle. In some embodiments of the process for purifying a diol mother liquor, one regeneration cycle is performed for every 100 (i) adsorption cycle/(ii) wash cycle/(iii) desorption cycle. In some embodiments of the process for purifying a diol mother liquor, one regeneration cycle is performed for every 50 (i) adsorption cycle/(ii) wash cycle/(iii) desorption cycle. In some embodiments of the process for purifying a diol mother liquor, one regeneration cycle is performed for every 40 (i) adsorption cycle/(ii) wash cycle/(iii) desorption cycle. In some embodiments of the process for purifying a diol mother liquor, one regeneration cycle is performed for every 30 (i) adsorption cycle/(ii) wash cycle/(iii) desorption cycle. In some embodiments of the process for purifying a diol mother liquor, one regeneration cycle is performed for every 20 (i) adsorption cycle/(ii) wash cycle/(iii) desorption cycle. In some embodiments of the process for purifying a diol mother liquor, one regeneration cycle is performed for every 10 (i) adsorption cycle/(ii) wash cycle/(iii) desorption cycle. In some embodiments of the process for purifying a diol mother liquor, one regeneration cycle is performed for every 5 (i) adsorption cycle/(ii) wash cycle/(iii) desorption cycle.

Also disclosed herein is a process for depolymerizing a polyester; the process comprising admixing the polyester with a mixture comprising an alkoxide; wherein the alkoxide is recovered from an alkoxide containing mother liquor using a process comprising:
(i) an adsorption cycle;
(ii) a wash cycle; and
(iii) a desorption cycle.

In some embodiment, the process for depolymerizing the polyester results in the formation of an organic diacid and a diol. In some embodiment, the process for depolymerizing the polyester results in the formation of a diester and a diol.

In some embodiment, the diol is mono ethylene glycol (MEG) (or ethylene glycol). In some embodiment, the diol is propylene glycol. In some embodiment, the diol is butylene glycol. In some embodiments, the diol is 1,4-cyclohexanedimethanol (1,4-bis(hydroxymethyl)cyclohexane). In some embodiments, the diol is 2,2,4,4-tetramethyl-1,3-cyclobutanediol. In some embodiments, the diacid is terephthalic acid. In some embodiments, the diacid is isophthalic acid. In some embodiments, the diester is dimethyl terephthalate (DMT). In some embodiments, the diester is dimethyl isophthalate (DMI).

In some embodiment, the polyester is selected from polyethylene terephthalate (PET), poly(ethylene glycol-co-1,4-cyclohexanedimethanol terephthalate) (PETG), polyglycolide or polyglycolic acid (PGA), polylactic acid (PLA), polycaprolactone (PCL), polyhydroxybutyrate (PHB), polyethylene adipate (PEA), polybutylene succinate (PBS), poly(3-hydroxybutyrate-co-3-hydroxyvalerate) (PHBV), polybutylene terephthalate (PBT), polytrimethylene terephthalate (PTT), polyethylene naphthalate (PEN), Vectran®, cutin, and any combinations thereof. In some embodiment, the polyester is polyethylene terephthalate (PET). In some embodiment, the polyester is poly(ethylene glycol-co-1,4-cyclohexanedimethanol terephthalate) (PETG).

In some embodiment, the process for depolymerizing polyethylene terephthalate (PET) results in the formation of a terephthalate and/or isophthalate, and mono ethylene glycol (MEG). In some embodiment, the terephthalate is dimethyl terephthalate. In some embodiment, the isophthalate is dimethyl isophthalate.

In some embodiment, the mixture comprising an alkoxide further comprises a solvent. In some embodiment, the solvent is methanol, ethanol, n-propanol, isopropanol, t-butanol, ethylene glycol, glycerol, cyclohexane-1,4-dimethanol, phenol, benzyl alcohol, or any combinations thereof. In some embodiment, the solvent is methanol.

In some embodiment, the adsorption cycle, wash cycle, and desorption cycle are performed sequentially. In some embodiment, the adsorption cycle and/or wash cycle and/or desorption cycle are performed continuously.

In some embodiment, the alkoxide containing mother liquor is obtained from a process of depolymerizing a polyester to form an organic diacid and a diol.

In some embodiment, the alkoxide containing mother liquor is obtained from a process of depolymerizing a polyester to form a diester and a diol.

In some embodiment, the diol is mono ethylene glycol (MEG) (or ethylene glycol). In some embodiment, the diol is propylene glycol. In some embodiments, the diol is butylene glycol. In some embodiments, the diol is 1,4-cyclohexanedimethanol (1,4-bis(hydroxymethyl)cyclohexane). In some embodiments, the diol is 2,2,4,4-tetramethyl-1,3-cyclobutanediol. In some embodiments, the diacid is terephthalic acid. In some embodiments, the diacid is isophthalic acid. In some embodiments, the diester is dimethyl terephthalate (DMT). In some embodiments, the diester is dimethyl isophthalate (DMI).

In some embodiment, the polyester is selected from polyethylene terephthalate (PET), poly(ethylene glycol-co-1,4-cyclohexanedimethanol terephthalate) (PETG), polyglycolide or polyglycolic acid (PGA), polylactic acid (PLA), polycaprolactone (PCL), polyhydroxybutyrate (PHB), polyethylene adipate (PEA), polybutylene succinate (PBS), poly (3-hydroxybutyrate-co-3-hydroxyvalerate) (PHBV), polybutylene terephthalate (PBT), polytrimethylene terephthalate (PTT), polyethylene naphthalate (PEN), Vectran®, cutin, and any combinations thereof. In some embodiment, the polyester is polyethylene terephthalate (PET). In some embodiment, the polyester is poly(ethylene glycol-co-1,4-cyclohexanedimethanol terephthalate) (PETG).

In some embodiment, the alkoxide containing mother liquor is obtained from a process of depolymerizing polyethylene terephthalate (PET) to form a terephthalate and/or isophthalate, and mono ethylene glycol (MEG).

In some embodiment, the terephthalate is dimethyl terephthalate. In some embodiment, the isophthalate is dimethyl isophthalate.

In some embodiment, the alkoxide containing mother liquor further comprises a diol. In some embodiment, the alkoxide containing mother liquor further comprises mono ethylene glycol (MEG).

Step (i): Adsorption Cycle

In some embodiment, the adsorption cycle comprises contacting the alkoxide containing mother liquor through an adsorbent, thereby adsorbing the alkoxide. In some embodiment, the adsorption cycle comprises eluting the alkoxide containing mother liquor through an adsorbent, thereby adsorbing the alkoxide.

In some embodiment, the eluting through the adsorbent is performed 1 to 20 times. In some embodiment, the eluting through the adsorbent is performed 1 to 15 times. In some embodiment, the eluting through the adsorbent is performed 1 to 10 times. In some embodiment, the eluting through the adsorbent is performed 1 to 5 times. In some embodiment, the eluting through the adsorbent is performed 1 to 3 times. In some embodiment, the eluting through the adsorbent is performed 20 times, 19 times, 18 times, 17 times, 16 times, 15 times, 14 times, 13 times, 12 times, 11 times, 10 times, 9 times, 8 times, 7 times, 6 times, 5 times, 4 times, 3 times, 2 times, or once.

In some embodiment, the eluting through the adsorbent is performed until at least between about 30% and about 99% of the alkoxide is adsorbed. In some embodiment, the eluting through the adsorbent is performed until at least between about 50% and about 99% of the alkoxide is adsorbed. In some embodiment, the eluting through the adsorbent is performed until at least between about 80% and about 99% of the alkoxide is adsorbed. In some embodiment, the eluting through the adsorbent is performed until at least between about 90% and about 99% of the alkoxide is adsorbed. In some embodiment, the eluting through the adsorbent is performed until at least about 30% of the alkoxide is adsorbed. In some embodiment, the eluting through the adsorbent is performed until at least about 40% of the alkoxide is adsorbed. In some embodiment, the eluting through the adsorbent is performed until at least about 50% of the alkoxide is adsorbed. In some embodiment, the eluting through the adsorbent is performed until at least about 60% of the alkoxide is adsorbed. In some embodiment, the eluting through the adsorbent is performed until at least about 70% of the alkoxide is adsorbed. In some embodiment, the eluting through the adsorbent is performed until at least about 80% of the alkoxide is adsorbed. In some embodiment, the eluting through the adsorbent is performed until at least about 90% of the alkoxide is adsorbed. In some embodiment, the eluting through the adsorbent is performed until at least about 95% of the alkoxide is adsorbed. In some embodiment, the eluting through the adsorbent is performed until at least about 99% of the alkoxide is adsorbed.

In some embodiments, the adsorbent is silica gel, a silicate derivative, $Al_2O_3$, polymeric alumina, zeolites, activated carbon, polysulfones, polysulfates, polycarboxylates, or any combinations thereof. In some embodiments, the silicate derivative is sepiolite, palygorskite, hydrotalcite, kaolinite, or diopside. In some embodiment, the adsorbent is silica gel with pore size between about 10 μm and about 800 μm. In some embodiment, the adsorbent is silica gel with specific surface area between about 20 $m^2/g$ and about 1000 $m^2/g$. In some embodiment, the adsorbent is basic alumina, neutral alumina, or acidic alumina. In some embodiment, the adsorbent is a mixture of alumina and silica gel. In some embodiment, the adsorbent is a mixture of zeolites and silica gel.

Step (ii): Wash Cycle

In some embodiment, the wash cycle comprises washing the adsorbent with a wash solvent. In some embodiment, the wash cycle comprises washing the surface of the adsorbent with a wash solvent. In some embodiment, the wash cycle comprises washing the adsorbent with a wash solvent, thereby eliminating ester salts, pigments, and dyes adsorbed during the adsorption cycle. In some embodiment, the ester salts, pigments, and dyes adsorbed during the adsorption cycle are adsorbed on the surface of the adsorbent. In some embodiment, the ester salts are monomethyl terephthalate or dimethyl terephthalate salts.

In some embodiment, the wash cycle is co-current or counter current. In some embodiment, the wash cycle is counter current. In some embodiment, the wash cycle is co-current.

In some embodiment, the washing is performed 1 to 20 times. In some embodiment, the washing is performed 1 to 15 times. In some embodiment, the washing is performed 1 to 10 times. In some embodiment, the washing is performed 1 to 5 times. In some embodiment, the washing is performed 1 to 3 times. In some embodiment, the washing is performed 20 times, 19 times, 18 times, 17 times, 16 times, 15 times, 14 times, 13 times, 12 times, 11 times, 10 times, 9 times, 8 times, 7 times, 6 times, 5 times, 4 times, 3 times, 2 times, or once.

In some embodiment, the washing is performed until at most between about 1% and about 30% of the alkoxide is desorbed from the adsorbent. In some embodiment, the washing is performed until at most between about 1% and about 20% of the alkoxide is desorbed from the adsorbent. In some embodiment, the washing is performed until at most between about 1% and about 10% of the alkoxide is desorbed from the adsorbent. In some embodiment, the washing is performed until at most between about 1% and about 5% of the alkoxide is desorbed from the adsorbent. In some embodiment, the washing is performed until at most about 30% of the alkoxide is desorbed from the adsorbent. In some embodiment, the washing is performed until at most about 25% of the alkoxide is desorbed from the adsorbent. In some embodiment, the washing is performed until at most about 20% of the alkoxide is desorbed from the adsorbent. In some embodiment, the washing is performed until at most about 15% of the alkoxide is desorbed from the adsorbent. In some embodiment, the washing is performed until at most about 10% of the alkoxide is desorbed from the adsorbent. In some embodiment, the washing is performed until at most about 5% of the alkoxide is desorbed from the adsorbent. In some embodiment, the washing is performed until at most about 1% of the alkoxide is desorbed from the adsorbent.

In some embodiment, the wash solvent is a polar protic solvent. In some embodiment, the wash solvent is a polar aprotic solvent. In some embodiment, the wash solvent is an apolar aprotic solvent. In some embodiment, the wash solvent is an alcoholic solvent. In some embodiments, the wash solvent is methanol, ethanol, propanol, butanol, or any combinations thereof. In some embodiments, the wash solvent is a mixture of an alcoholic solvent and a polar solvent. In some embodiments, the wash solvent is a mixture of an alcoholic solvent and an apolar solvent. In some embodiments, the wash solvent is methanol. In some embodiments, the wash solvent is methanol and cyclohexane. In some embodiments, the wash solvent is methanol and acetonitrile. In some embodiments, the wash solvent is cyclohexane/mono ethylene glycol/methanol.

Step (iii): Desorption Cycle

In some embodiment, the desorption cycle comprises washing the adsorbent with a desorption solvent, thereby obtaining a mixture comprising the alkoxide and the desorption solvent.

In some embodiment, the washing to obtain the mixture comprising the alkoxide and the desorption solvent is performed 1 to 20 times. In some embodiment, the washing to obtain the mixture comprising the alkoxide and the desorption solvent is performed 1 to 15 times. In some embodiment, the washing to obtain the mixture comprising the alkoxide and the desorption solvent is performed 1 to 10 times. In some embodiment, the washing to obtain the mixture comprising the alkoxide and the desorption solvent is performed 1 to 5 times. In some embodiment, the washing to obtain the mixture comprising the alkoxide and the desorption solvent is performed 1 to 3 times. In some embodiment, the washing to obtain the mixture comprising the alkoxide and the desorption solvent is performed 20 times, 19 times, 18 times, 17 times, 16 times, 15 times, 14 times, 13 times, 12 times, 11 times, 10 times, 9 times, 8 times, 7 times, 6 times, 5 times, 4 times, 3 times, 2 times, or once.

In some embodiment, the washing to obtain the mixture comprising the alkoxide and the desorption solvent is performed until at least between about 30% and about 99% of the alkoxide is desorbed from the adsorbent. In some embodiment, the washing to obtain the mixture comprising the alkoxide and the desorption solvent is performed until at least between about 50% and about 99% of the alkoxide is desorbed from the adsorbent. In some embodiment, the washing to obtain the mixture comprising the alkoxide and the desorption solvent is performed until at least between about 90% and about 99% of the alkoxide is desorbed from the adsorbent. In some embodiment, the washing to obtain the mixture comprising the alkoxide and the desorption solvent is performed until at least about 30% of the alkoxide is desorbed from the adsorbent. In some embodiment, the washing to obtain the mixture comprising the alkoxide and the desorption solvent is performed until at least about 40% of the alkoxide is desorbed from the adsorbent. In some embodiment, the washing to obtain the mixture comprising the alkoxide and the desorption solvent is performed until at least about 50% of the alkoxide is desorbed from the adsorbent. In some embodiment, the washing to obtain the mixture comprising the alkoxide and the desorption solvent is performed until at least about 60% of the alkoxide is desorbed from the adsorbent. In some embodiment, the washing to obtain the mixture comprising the alkoxide and the desorption solvent is performed until at least about 70% of the alkoxide is desorbed from the adsorbent. In some embodiment, the washing to obtain the mixture comprising the alkoxide and the desorption solvent is performed until at least about 80% of the alkoxide is desorbed from the adsorbent. In some embodiment, the washing to obtain the mixture comprising the alkoxide and the desorption solvent is performed until at least about 90% of the alkoxide is desorbed from the adsorbent. In some embodiment, the washing to obtain the mixture comprising the alkoxide and the desorption solvent is performed until at least about 95% of the alkoxide is desorbed from the adsorbent. In some embodiment, the washing to obtain the mixture comprising the alkoxide and the desorption solvent is performed until at least about 99% of the alkoxide is desorbed from the adsorbent.

In some embodiment, the washing to obtain the mixture comprising the alkoxide and the desorption solvent is performed at room temperature. In some embodiment, the washing to obtain the mixture comprising the alkoxide and the desorption solvent is performed at elevated temperature. In some embodiment, the washing to obtain the mixture comprising the alkoxide and the desorption solvent is performed at about 30° C., about 35° C., about 40° C., about 45° C., about 50° C., about 55° C., about 60° C., about 65° C., or about 70° C.

In some embodiment, the desorption solvent is a polar protic solvent. In some embodiment, the desorption solvent is a polar aprotic solvent. In some embodiment, the desorption solvent is an apolar aprotic solvent. In some embodiment, the desorption solvent is an alcoholic solvent. In some embodiments, the desorption solvent is methanol, ethanol, propanol, butanol, or any combinations thereof. In some embodiments, the desorption solvent is a mixture of an alcoholic solvent and a polar solvent. In some embodiments, the desorption solvent is a mixture of an alcoholic solvent and an apolar solvent. In some embodiments, the desorption solvent is methanol. In some embodiments, the desorption solvent is methanol and cyclohexane. In some embodiments, the desorption solvent is methanol and acetonitrile. In some embodiments, the desorption solvent is cyclohexane/mono ethylene glycol/methanol.

In some embodiment, a portion of the desorption solvent in the mixture comprising the alkoxide and the desorption solvent is subsequently removed. In some embodiments, a portion of the desorption solvent is removed under vacuum. In some embodiments, a portion of the desorption solvent is removed under pressure.

In some embodiment, the final concentration of the alkoxide in the desorption solvent is between about 0.1 wt-% to about 100 wt-%. In some embodiment, the final concentration of the alkoxide in the desorption solvent is between about 0.1 wt-% to about 90 wt-%. In some embodiment, the final concentration of the alkoxide in the desorption solvent is between about 0.1 wt-% to about 80 wt-%. In some embodiment, the final concentration of the alkoxide in the desorption solvent is between about 0.1 wt-% to about 70 wt-%. In some embodiment, the final concentration of the alkoxide in the desorption solvent is between about 0.1 wt-% to about 60 wt-%. In some embodiment, the final concentration of the alkoxide in the desorption solvent is between about 0.1 wt-% to about 50 wt-%. In some embodiment, the final concentration of the alkoxide in the desorption solvent is between about 0.1 wt-% to about 40 wt-%. In some embodiment, the final concentration of the alkoxide in the desorption solvent is between about 0.1 wt-% to about 30 wt-%. In some embodiment, the final concentration of the alkoxide in the desorption solvent is between about 0.1 wt-% to about 20 wt-%. In some embodiment, the final concentration of the alkoxide in the desorption solvent is between about 0.1 wt-% to about 10 wt-%.

In some embodiment, the alkoxide in the desorption solvent is further re-used in a process of depolymerizing a polyester to form an organic diacid and a diol. In some embodiment, the alkoxide in the desorption solvent is further re-used in a process of depolymerizing a polyester to form a diester and a diol. In some embodiment, the diol is mono ethylene glycol (MEG) (or ethylene glycol). In some embodiment, the diol is propylene glycol. In some embodiment, the diol is butylene glycol. In some embodiments, the diol is 1,4-cyclohexanedimethanol (1,4-bis(hydroxymethyl) cyclohexane). In some embodiments, the diol is 2,2,4,4-tetramethyl-1,3-cyclobutanediol. In some embodiments, the diacid is terephthalic acid. In some embodiments, the diacid is isophthalic acid. In some embodiments, the diester is dimethyl terephthalate (DMT). In some embodiments, the diester is dimethyl isophthalate (DMI).

In some embodiment, the polyester is selected from polyethylene terephthalate (PET), poly(ethylene glycol-co-1,4-cyclohexanedimethanol terephthalate) (PETG), polyglycolide or polyglycolic acid (PGA), polylactic acid (PLA), polycaprolactone (PCL), polyhydroxybutyrate (PHB), polyethylene adipate (PEA), polybutylene succinate (PBS), poly(3-hydroxybutyrate-co-3-hydroxyvalerate) (PHBV), polybutylene terephthalate (PBT), polytrimethylene terephthalate (PTT), polyethylene naphthalate (PEN), Vectran®, cutin, and any combinations thereof. In some embodiment, the polyester is polyethylene terephthalate (PET). In some embodiment, the polyester is poly(ethylene glycol-co-1,4-cyclohexanedimethanol terephthalate) (PETG).

In some embodiment, the alkoxide in the desorption solvent is further re-used in a process of depolymerizing polyethylene terephthalate (PET) to form a terephthalate and/or an isophthalate, and mono ethylene glycol (MEG). In some embodiment, the terephthalate is dimethyl terephthalate. In some embodiment, the isophthalate is dimethyl isophthalate.

In some embodiment, the alkoxide is alkali metal alkoxide, an alkaline earth metal alkoxide, a metal alkoxide, an ammonium alkoxide, or any combinations thereof. In some embodiment, the alkoxide is sodium methoxide, sodium glycoxide, potassium ethoxide, aluminum tri-n-propoxide, tetrabutylammonium methoxide, or any combinations thereof. In some embodiment, the alkoxide is sodium methoxide. In some embodiment, the alkoxide is sodium glycoxide.

In some embodiment, the process for the recovery of the alkoxide further comprises (iv) a regeneration cycle.

In some embodiment, the process comprises:
(i) an adsorption cycle;
(ii) a wash cycle;
(iii) a desorption cycle; and
(iv) a regeneration cycle.

Step (iv): Regeneration Cycle

In some embodiment, the regeneration cycle comprises washing the adsorbent with an acid, thereby regenerating the adsorbent.

In some embodiment, the washing is performed 1 to 20 times. In some embodiment, the washing is performed 1 to 15 times. In some embodiment, the washing is performed 1 to 10 times. In some embodiment, the washing is performed 1 to 5 times. In some embodiment, the washing is performed 1 to 3 times. In some embodiment, the washing is performed 20 times, 19 times, 18 times, 17 times, 16 times, 15 times, 14 times, 13 times, 12 times, 11 times, 10 times, 9 times, 8 times, 7 times, 6 times, 5 times, 4 times, 3 times, 2 times, or once.

In some embodiment, the acid is acetic acid, formic acid, hydrochloric acid, sulfuric acid, phosphoric acid, or any combinations thereof. In some embodiment, the acid is acetic acid.

In some embodiment, the acid is formic acid.

In some embodiment, one regeneration cycle is performed for every 5 to 100 (i) adsorption cycle/(ii) wash cycle/(iii) desorption cycle. In some embodiment, one regeneration cycle is performed for every 25 to 100 (i) adsorption cycle/(ii) wash cycle/(iii) desorption cycle. In some embodiment, one regeneration cycle is performed for every 50 to 100 (i) adsorption cycle/(ii) wash cycle/(iii) desorption cycle. In some embodiment, one regeneration cycle is performed for every 100 (i) adsorption cycle/(ii) wash cycle/(iii) desorption cycle. In some embodiment, one regeneration cycle is performed for every 50 (i) adsorption cycle/(ii) wash cycle/(iii) desorption cycle. In some embodiment, one regeneration cycle is performed for every 40 (i) adsorption cycle/(ii) wash cycle/(iii) desorption cycle. In some embodiment, one regeneration cycle is performed for every 30 (i) adsorption cycle/(ii) wash cycle/(iii) desorption cycle. In some embodiment, one regeneration cycle is performed for every 20 (i) adsorption cycle/(ii) wash cycle/(iii) desorption cycle. In some embodiment, one regeneration cycle is performed for every 10 (i) adsorption cycle/(ii) wash cycle/(iii) desorption cycle. In some embodiment, one regeneration cycle is performed for every 5 (i) adsorption cycle/(ii) wash cycle/(iii) desorption cycle.

Certain Terminology

The section headings used herein are for organizational purposes only and are not to be construed as limiting the subject matter described.

Unless defined otherwise, all technical and scientific terms used herein have the same meaning as is commonly understood to which the claimed subject matter belongs. In the event that there are a plurality of definitions for terms herein, those in this section prevail.

It is to be understood that the general description and the detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

Unless the context requires otherwise, throughout the specification and claims which follow, the word "comprise" and variations thereof, such as, "comprises" and "comprising" are to be construed in an open, inclusive sense, that is, as "including, but not limited to." Further, headings provided herein are for convenience only and do not interpret the scope or meaning of the claimed invention.

As used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

As used herein, the term "about" or "approximately" means within 10%, preferably within 10%, and more preferably within 5% of a given value or range.

As used herein, ambient temperature is a colloquial expression for the typical or preferred indoor (climate-controlled) temperature to which people are generally accustomed. It represents the small range of temperatures at which the air feels neither hot nor cold, approximately 21° C. In some embodiments, ambient temperature is 25±5° C. In some embodiments, ambient temperature is 18° C. In some embodiments, ambient temperature is 19° C. In some embodiments, ambient temperature is 20° C. In some embodiments, ambient temperature is 21° C. In some embodiments, ambient temperature is 22° C. In some embodiments, ambient temperature is 23° C. In some embodiments, ambient temperature is 24° C. In some embodiments, ambient temperature is 25° C. In some embodiments, ambient temperature is 26° C. In some embodiments, ambient temperature is 27° C. In some embodiments, ambient temperature is 28° C. In some embodiments, ambient temperature is 29° C. In some embodiments, ambient temperature is 30° C.

As used in this specification and the appended claims, depolymerization, refer to a way of breaking down a polymer to its starting material. It is essentially the opposite of polymerization. In some embodiments, the depolymerization is achieved by glycolysis, methanolysis, or hydrolysis, categorized by the depolymerization reactant used, such as glycol, methanol or water, respectively.

As used herein, the term "mol" when referring to PET is the molar amount and is calculated using the molecular weight of the "PET" unit which is 192.17 g/mol.

Definition of standard chemistry terms may be found in reference works, including but not limited to, Carey and Sundberg "Advanced Organic Chemistry $4^{th}$ Ed." Vols. A (2000) and B (2001), Plenum Press, New York.

As used herein, the term "counter current" means that the solvent flow runs in the opposite direction.

As used herein, the term "co-current" means that the solvent flow runs in the same direction.

EXAMPLES

The following examples are intended to illustrate but not limit the disclosed embodiments.

Flow rates were the same for all examples: 400 g/min for adsorption cycles, and 40 g/min for wash and desorption cycles.

Example 1: Adsorption on Silica Gel, Wash and Desorption with Methanol

A chromatography column was charged with 500 g of silica gel ($SiO_2$). Then 2000 g of mother liquor containing 1.4 wt-% of sodium methoxide was eluted through the adsorbent, after which the mother liquor contained only traces of methoxide: 0.01 wt-%. The adsorbent was then washed with 500 g methanol (99.8% purity), removing dyes as well as of methoxide (1.1 wt-% vs adsorbent, 4.0 wt-% of total adsorbed methoxide).

Sodium methoxide desorption was performed by eluting 2000 g of methanol to yield 1.5 wt-% of methoxide in methanol.

The whole process was performed at 20° C. It was repeated 11 times on the same silica gel with final methoxide concentration in methanol at 1.2 wt-%.

The methoxide solution was concentrated to 10 wt-% by evaporation under vacuum, and used in a depolymerization of poly(ethylene terephthalate), with a DMT yield of 96%.

Example 2: Adsorption on a Mixture of Sepiolite and Silica Gel, Wash and Desorption with Methanol A chromatography column, charged with a mixture of sepiolite (250 g) and silica gel (250 g), was eluted with 2000 g of mother liquor containing 1.4 wt-% of sodium methoxide. The resulting mother liquor did not contain any methoxide (pH 7).

The adsorbent was washed with 500 g of methanol to yield a solution containing 0.86 wt-% of methoxide. Desorption was done 3 times: the first one with 250 g methanol gave a solution of 0.86 wt-% of methoxide; the second one with 100 g methanol, a solution of 1.1 wt-% of methoxide; the third one with 75 g of methanol, a solution of 0.85 wt-% of methoxide. All was performed at 20° C.

Example 3: Adsorption on a Mixture of Sepiolite and Silica Gel, Wash and Desorption with a Mixture of Cyclohexane, Mono Ethylene Glycol, and Methanol Same as Example 2 except the desorption was performed with a mixture of cyclohexane/mono ethylene glycol/methanol in a weight ratio of 22/8/70. The resulting solution contained 1.72 wt-% of methoxide.

Example 4: Adsorption on Basic Alumina, Wash and Desorption with Methanol

Same as Example 1 except the adsorbent is basic alumina. Sodium methoxide desorption was performed by eluting 2000 g of methanol to yield 0.9 wt-% of methoxide in methanol.

Example 5: Desorption at Elevated Temperature

Same as Example 1 except for the desorption temperature. Sodium methoxide desorption was performed at 55° C. by eluting 2000 g of methanol to yield 1.7 wt-% of methoxide in methanol.

Example 6: Adsorbent Recovery

Silica gel adsorbent used in Example 1 was recovered by washing it at 20° C. with 150 g of a 0.5 wt-% acetic acid aqueous solution, followed by washing, also at 20° C., with 1000 g of deionized water until pH=7.5. After drying at 140° C. for 24 h, the silica gel was then ready for reuse.

What is claimed is:
1. A process for depolymerizing a polyester, wherein the process comprises admixing the polyester with a mixture comprising an alkoxide; wherein the alkoxide is recovered from an alkoxide containing mother liquor using a process comprising:
- (i) an adsorption cycle;
- (ii) a wash cycle; and
- (iii) a desorption cycle.

2. The process of claim 1, wherein the polyester is polyethylene terephthalate (PET).

3. The process of claim 1, wherein the adsorption cycle comprises contacting the alkoxide containing mother liquor with an adsorbent, thereby adsorbing the alkoxide.

4. The process of claim 3, wherein the wash cycle comprises washing the adsorbent with a wash solvent, thereby eliminating ester salts, pigments, and/or dyes adsorbed during the adsorption cycle.

5. The process of claim 3, wherein the desorption cycle comprises washing the adsorbent with a desorption solvent, thereby obtaining a mixture comprising the alkoxide and the desorption solvent.

6. The process of claim 5, wherein the washing is performed until at least about 30% of the alkoxide is desorbed from the adsorbent.

7. The process of claim 1, wherein the polyester comprises polyethylene terephthalate (PET) and the depolymerizing forms a terephthalate, and mono ethylene glycol (MEG).

8. The process of claim 1, wherein the alkoxide is sodium methoxide, sodium glycoxide, potassium ethoxide, aluminum tri-n-propoxide, tetrabutylammonium methoxide, or any combinations thereof.

9. The process of claim 1, wherein the alkoxide is sodium methoxide.

10. The process of claim 1, wherein the alkoxide is sodium glycoxide.

11. A system for recovering an alkoxide from an alkoxide containing mother liquor, the system comprising:
- (i) an alkoxide containing mother liquor;
- (ii) an adsorbent;
- (iii) a wash solvent; and
- (iv) a desorption solvent.

12. The system of claim 11, wherein the alkoxide containing mother liquor further comprises a diol.

13. The system of claim 11, wherein the alkoxide containing mother liquor further comprises mono ethylene glycol (MEG).

14. The system of claim 11, wherein the adsorbent is silica gel, a silicate derivative, $Al_2O_3$, polymeric alumina, zeolites, activated carbon, polysulfones, polysulfates, polycarboxylates, or any combinations thereof.

15. The system of claim 11, wherein the wash solvent is a protic solvent.

16. The system of claim 11, wherein the wash solvent is an alcoholic solvent.

17. The system of claim 11, wherein the wash solvent is methanol.

18. The system of claim 11, wherein the desorption solvent is a protic solvent.

19. The system of claim 11, wherein the desorption solvent is an alcoholic solvent.

20. The system of claim 11, wherein the desorption solvent is methanol.

21. The system of claim 11, wherein the wash solvent is an aprotic solvent.

22. The system of claim 11, wherein the desorption solvent is an aprotic solvent.

* * * * *